(12) United States Patent
Graupe et al.

(10) Patent No.: US 8,673,966 B2
(45) Date of Patent: Mar. 18, 2014

(54) ALDH-2 INHIBITORS IN THE TREATMENT OF ADDICTION

(75) Inventors: Michael Graupe, Pacifica, CA (US); Chandrasekar Venkataramani, Redwood City, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 23 days.

(21) Appl. No.: 13/599,368

(22) Filed: Aug. 30, 2012

(65) Prior Publication Data

US 2013/0231325 A1   Sep. 5, 2013

Related U.S. Application Data

(60) Provisional application No. 61/529,164, filed on Aug. 30, 2011.

(51) Int. Cl.
*C07D 311/36* (2006.01)
*A61K 31/353* (2006.01)
*A61P 25/30* (2006.01)

(52) U.S. Cl.
USPC ............................ 514/456; 549/402; 549/403

(58) Field of Classification Search
USPC ................... 514/456; 549/402, 403
See application file for complete search history.

(56) References Cited

FOREIGN PATENT DOCUMENTS

| WO | WO-9958124 A1 | 11/1999 |
| WO | WO-2006011669 A1 | 2/2006 |
| WO | WO-2009094028 A1 | 7/2009 |

OTHER PUBLICATIONS

Arolfo, Maria P. et al. (2009) "Suppression of Heavy Drinking and Alcohol Seeking by a Selective ALDH-2 Inhibitor" *Alcoholism: Clinical and Experimental Research* 33(11):1935-1944.
Overstreet, D. et al (2009) "A Selective ALDH-2 Inhibitor Reduces Anxiety in Rats" *Pharmacology, Biochemistry and Behavior* 94:255-261.
Shippenberg, Toni S. et al. (2002) "Recent Advances in Animal Models of Drug Addiction" *Neuropsychopharmacology: The Fifth Generation of Progress* 97: 1381-1397.
Yao, L. et al. (2010) "Inhibition of Aldehyde Dehydrogenase-2 Suppresses Cocaine Seeking by Generating THP, a Cocaine Use-Dependent Inhibitor of Dopamine Synthesis" *Nature Medicine* 16(9):1024-1031.
International Search Report for PCT/US2012/053110, International Filing Date Aug. 30, 2012, mailed Dec. 5, 2012.

*Primary Examiner* — Sreeni Padmanabhan
*Assistant Examiner* — Irina Neagu
(74) *Attorney, Agent, or Firm* — Francis O. Ginah; J. Elin Hartrum

(57) ABSTRACT

Disclosed are novel isoflavone derivatives having the structure of Formula I:

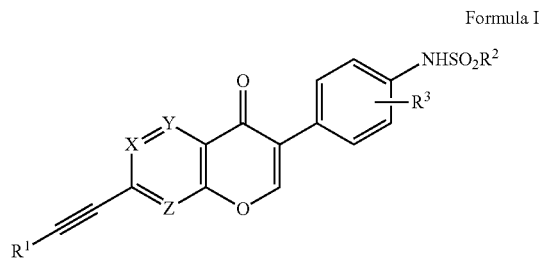

Figure 1:
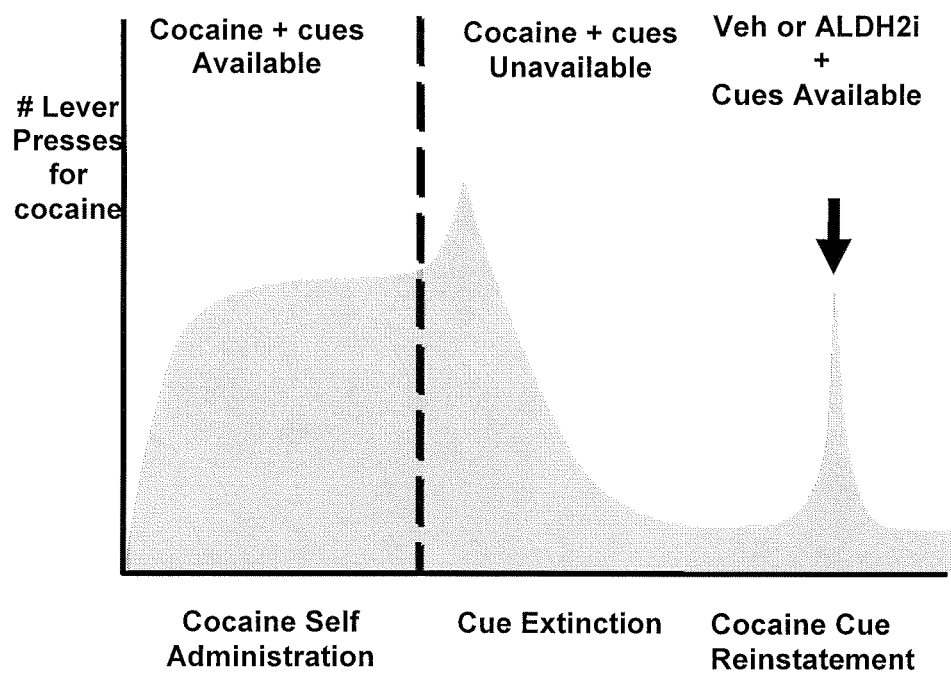

which are ALDH-2 inhibitors, useful for treating a patient in need thereof, for dependence upon drugs of addiction, for example addiction to dopamine-producing agent such as cocaine, morphine, amphetamines, nicotine, and alcohol.

30 Claims, 2 Drawing Sheets

Cocaine cue reinstatement study design

Oral compound of Example 6A significantly inhibited cocaine cue reinstatement

<u>Vehicle</u>: Formulation 2B- 4 ml/kg;  # p<0.01 vs Extinction **p<0.01 vs Vehicle

ALDH-2 INHIBITORS IN THE TREATMENT OF ADDICTION

CROSS-REFERENCE TO RELATED APPLICATIONS

This application claims benefit under 35 U.S.C. §119(e) to U.S. Provisional Application Ser. No. 61/529,164, filed on Aug. 30, 2011, the entirety of which is incorporated herein by reference.

FIELD OF THE INVENTION

The present invention relates to novel ALDH-2 inhibitors, and to their use in treating patients in need thereof, for dependence upon drugs or substances of addiction, for example addiction to dopamine-producing agent such as cocaine, opiates, amphetamines, nicotine, and alcohol. ALDH-2 inhibitors have also been shown to be effective in treating obesity. The invention also relates to pharmaceutical compositions containing compounds of the invention.

BACKGROUND

Today, dependence upon drugs of addiction causes major health problems worldwide. For example, alcohol abuse and alcohol dependency can cause liver, pancreatic and kidney disease, heart disease, including dilated cardiomyopathy, polyneuropathy, internal bleeding, brain deterioration, alcohol poisoning, increased incidence of many types of cancer, insomnia, depression, anxiety, and even suicide. Heavy alcohol consumption by a pregnant mother can also lead to fetal alcohol syndrome, which is an incurable condition. Additionally, alcohol abuse and alcohol dependence are major contributing factors for head injuries, motor vehicle accidents, violence and assaults, and other neurological and other medical problems.

Addiction to nicotine is estimated by the National Institute on Drug Abuse to kill nearly 500,000 Americans every year. This total represents about 1 in 6 of all deaths in the U.S. caused by any means, and is more than the total of deaths caused by use of alcohol, cocaine, heroin, suicide, car accidents, fire and AIDS combined. Cigarette smoking is the most popular method of using nicotine, but here are smokeless tobacco products; for example, snuff, chewing tobacco.

Nicotine addiction is linked to disease states such as leukemia, cataracts, and pneumonia; and is the cause of about one-third of all cancer deaths, the foremost of which is lung cancer. In addition to cancer, cigarette smoking also causes lung diseases, such as bronchitis and emphysema, exacerbates asthma symptoms, and is the cause of chronic obstructive pulmonary diseases in general. It is also well known that cigarette smoking increases the risk of cardiovascular diseases, including stroke, heart attack, vascular disease, aneurysm, and the like.

Another major health problem is caused by cocaine abuse. Physical effects of cocaine use include constricted blood vessels, dilated pupils, and increased temperature, heart rate, and blood pressure. A user of cocaine can experience acute cardiovascular or cerebrovascular emergencies, such as a heart attack or stroke, potentially resulting in sudden death. Other complications associated with cocaine use include disturbances in heart rhythm, chest pain and respiratory failure, seizures and headaches, and gastrointestinal complications such as abdominal pain and nausea. Because cocaine has a tendency to decrease appetite, many chronic users can become malnourished. Repeated use of cocaine may lead to a state of increasing irritability, restlessness, and paranoia. This can result in a period of full-blown paranoid psychosis, in which the user loses touch with reality and experiences auditory hallucinations.

Moreover, it is well known that the concurrent abuse of nicotine, cocaine and alcohol is common. It has been found that the combination of cocaine and alcohol exerts more cardiovascular toxicity than either drug alone in humans.

Historically, treating chemical dependence largely involved attempts to persuade patients to voluntarily discontinue use of the substance(s) (behavioral therapy). However, cocaine, morphine, amphetamines, nicotine, alcohol, and other types of dopamine-producing agents are highly addictive substances, and dependence upon such drugs can be harder to break and significantly more damaging than dependence on most other addictive substances. In particular, alcohol, cocaine, and heroin dependence are typically seen to be chronic relapsing disorders. There has been some moderate success in providing effective treatments for tobacco addiction by the use of nicotine replacement therapy, such as nicotine gum or the nicotine transdermal patch. Additionally, antidepressants and antihypertensive drugs have been tried, with modest success. Attempts have also been made to treat tobacco addiction by persuading patients to discontinue the use of tobacco voluntarily (behavioral therapy), but this method has not proved to be very successful. Accordingly, it is clearly desirable to find a treatment for tobacco addiction that reduces or prevents the craving for nicotine and does not involve nicotine replacement therapy or the use of antidepressants and antihypertensive drugs.

Accordingly, there has been much interest in the scientific community in attempting to find substances that could be employed to ameliorate dependency on addictive agents. Two compounds that have previously been employed for the treatment of alcohol abuse are known as disulfiram (Antabuse™) and cyanamide. Additionally, it has been recently proposed that disulfiram can be used for the treatment of cocaine dependency (for example, see Bonet et al., Journal of Substance Abuse Treatment, 26 (2004), 225-232).

More recently it has been shown that a compound known as daidzein is effective in suppressing ethanol intake. Daidzein is the major active component obtained from extracts of Radix puerariae, a traditional Chinese medication that suppresses ethanol intake in Syrian golden hamsters. See Keung, W. M. and Vallee, B. L. (1993) Proc. Natl. Acad. Sci. USA 90, 10008-10012 and Keung, W. M., Klyosov, A. A., and Vallee, B. L. (1997) Proc. Natl. Acad. Sci. USA 94, 1675-1679, and U.S. Pat. Nos. 5,624,910 and 6,121,010.

It has been shown that daidzin is an isoflavone of the formula:

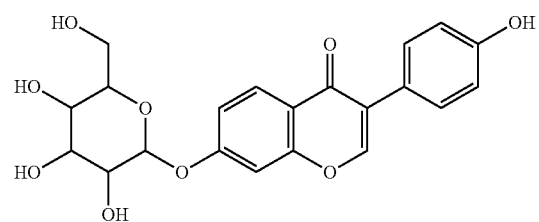 [SMILES: O=c1c(-c2ccc(O)cc2)coc2cc(OC3OC(CO)C(O)C(O)C3O)ccc12]

Removal of the sugar provides a compound known as daidzein, which has also been shown to be effective in suppressing ethanol uptake.

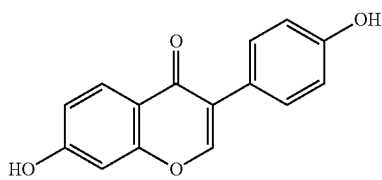 [SMILES: O=c1c(-c2ccc(O)cc2)coc2cc(O)ccc12]

U.S. Pat. Nos. 5,624,910 and 6,121,010 disclosed ether derivatives of daidzin, which were shown to be effective in treating ethanol dependency. Daidzin and its analogs were shown to be potent and selective inhibitors of human mitochondrial aldehyde dehydrogenase (ALDH-2), which is an enzyme involved in the major enzymatic pathway responsible for ethanol metabolism in humans. It was also found that daidzin analogues that inhibit ALDH-2 but also inhibit the monoamine oxidase (MOA) pathway were the least effective antidipsotropic activity.

In U.S. Patent Application Ser. No. 60/834,083, novel isoflavone derivatives were disclosed that are ALDH-2 inhibitors with little effect on the MOA pathway, and are useful for the treatment of alcohol dependency. It has now surprisingly been found that ALDH-2 inhibitors are also useful for the treatment of other addictive agents such as cocaine, heroin, and nicotine, and in particular, ameliorate the tendency of abusers to relapse.

SUMMARY OF THE INVENTION

Accordingly, in a first aspect, the invention relates to compounds of Formula I:

Formula I

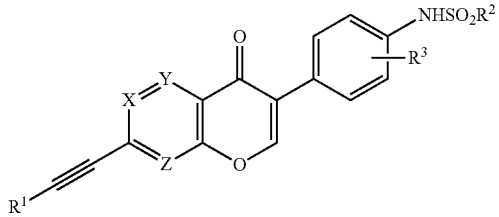

wherein:
  $R^1$ is optionally substituted alkyl, optionally substituted cycloalkyl, optionally substituted heterocyclyl, optionally substituted heteroaryl, or optionally substituted phenyl;
  $R^2$ is hydrogen, optionally substituted alkyl, optionally substituted cycloalkyl, or optionally substituted phenyl;
  $R^3$ is hydrogen, cyano, optionally substituted amino, alkyl, alkoxy, or halo; and
  X, Y and Z are chosen from —$CR^4$— and —N—, in which $R^4$ is hydrogen, alkyl, lower alkoxy, or halo; or a pharmaceutically acceptable salt thereof.

In a second aspect of the invention, pharmaceutical formulations are provided comprising a therapeutically effective amount of an ALDH-2 inhibitor of Formula I and at least one pharmaceutically acceptable carrier.

In a third aspect of the invention, methods of using the compounds of Formula I in the treatment of addiction to dopamine-producing agents are provided. The method comprises administering to a patient in need thereof a therapeutically effective dose of a compound of Formula I. Such diseases include, but are not limited to, the treatment of dependency upon cocaine, opiates, amphetamines, nicotine, alcohol and excessive food intake.

Accordingly, in one embodiment, the invention relates to compounds of Formula I:

Formula I

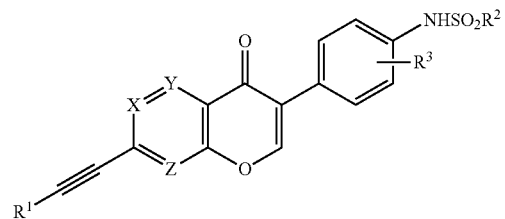

wherein:
  $R^1$ is optionally substituted alkyl, optionally substituted cycloalkyl, optionally substituted heterocyclyl, optionally substituted heteroaryl, or optionally substituted phenyl;
  $R^2$ is hydrogen, optionally substituted lower alkyl, optionally substituted cycloalkyl, or optionally substituted phenyl;
  $R^3$ is hydrogen, cyano, optionally substituted amino, lower alkyl, lower alkoxy, or halo; and
  X, Y and Z are chosen from —$CR^4$— and —N—, in which $R^4$ is hydrogen, lower alkyl, lower alkoxy, or halo; and the pharmaceutically acceptable salts thereof.

In one embodiment, the invention relates to compounds of Formula I in which $R^1$ is optionally substituted alkyl and $R^2$ is optionally substituted alkyl or optionally substituted cycloalkyl, particularly where $R^1$ is alkyl of 1-6 carbon atoms optionally substituted by halo, hydroxyl, cyano, optionally substituted alkoxy of 1-6 carbon atoms, optionally substituted acyl, optionally substituted amino, optionally substituted carboxylalkyl, optionally substituted carboxylcycloalkyl, or optionally substituted alkoxycarbonylamino, and X, Y and Z are —$CR^4$— and $R^3$ is hydrogen.

In another embodiment, the invention relates to compounds of Formula I in which $R^1$ is optionally substituted cycloalkyl and $R^2$ is optionally substituted alkyl or optionally substituted cycloalkyl, particularly where $R^1$ is cycloalkyl of 3-6 carbon atoms optionally substituted by halo, hydroxyl, cyano, alkoxy of 1-6 carbon atoms, optionally substituted acyl, optionally substituted amino, optionally substituted carboxylalkyl, optionally substituted carboxylcycloalkyl, or optionally substituted alkoxycarbonylamino, and X, Y and Z are —$CR^4$— and $R^3$ is hydrogen.

In another embodiment, the invention relates to compounds of Formula I in which $R^1$ is optionally substituted heteroaryl and $R^2$ is optionally substituted alkyl or optionally substituted cycloalkyl, particularly where $R^1$ is heteroaryl optionally substituted by halo, hydroxyl, cyano, alkoxy of 1-6 carbon atoms, optionally substituted acyl, optionally substituted amino, optionally substituted carboxylalkyl, optionally substituted carboxylcycloalkyl, or optionally substituted alkoxycarbonylamino, and X, Y and Z are —$CR^4$— and $R^3$ is hydrogen.

In another embodiment, the invention relates to compounds of Formula I in which $R^1$ is optionally substituted phenyl, $R^2$ is optionally substituted alkyl or optionally substituted cycloalkyl, and $R^3$ is hydrogen.

In yet another embodiment, the invention relates to a method for the manufacture of a medicament for treating chemical dependency comprising administering a therapeutically effective dose of a compound of the invention to a patient in need thereof.

In yet another embodiment, the invention relates to compounds of Formula I in which $R^1$ is optionally substituted heterocyclyl and $R^2$ is optionally substituted alkyl or optionally substituted cycloalkyl, particularly X, Y and Z are —$CR^4$— and $R^3$ is hydrogen. In one class $R^1$ is optionally substituted piperidine or optionally substituted tetrahydropyran. In a second class $R^1$ is optionally substituted azetidine, in particular N-substituted azetidine, wherein the N-substitution is chosen from optionally substituted alkyl of 1-6 carbon atoms, optionally substituted acyl, optionally substituted amino, optionally substituted carboxylalkyl, optionally substituted carboxylcycloalkyl, and optionally substituted alkoxycarbonylamino.

In yet another embodiment, the invention relates to a method of treating chemical dependency on a dopamine-producing agent, comprising administering a therapeutically effective dose of the compound of the invention to a patient in need thereof.

In yet another embodiment, the invention relates to a method of treating chemical dependency on a dopamine-producing agent wherein the dopamine-producing agent is selected from the group consisting of cocaine, opiates, amphetamines, nicotine, and alcohol.

In yet another embodiment, the present invention provides a pharmaceutical composition comprising a therapeutically effective amount of a compound of the invention and one or more pharmaceutically acceptable carriers or diluents.

In yet another embodiment, the present invention provides a compound according to the invention or a pharmaceutically acceptable salt thereof, for use in therapy.

In yet another embodiment, the present invention provides the use of a compound according to the invention or a pharmaceutically acceptable salt thereof, for the manufacture of a medicament for treating chemical dependency.

In yet another embodiment, the invention relates to compounds of Formula I:

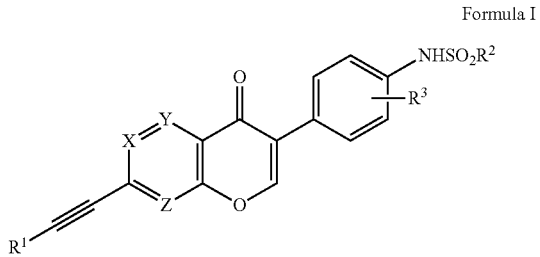

Formula I wherein:
  $R^1$ is optionally substituted alkyl, optionally substituted cycloalkyl, optionally substituted heterocyclyl, optionally substituted heteroaryl, or optionally substituted phenyl;
  $R^2$ is hydrogen, optionally substituted lower alkyl, optionally substituted cycloalkyl, or optionally substituted phenyl;
  $R^3$ is hydrogen, cyano, optionally substituted amino, lower alkyl, lower alkoxy, or halo; and
  X, Y and Z are chosen from —$CR^4$— and —N—, in which $R^4$ is hydrogen, lower alkyl, lower alkoxy, or halo; and pharmaceutically acceptable salts thereof.

Compounds for use in the invention include, but are not limited to:
N-(4-(7-(3-hydroxy-3-methylbut-1-ynyl)-4-oxo-4H-chromen-3-yl)phenyl)methanesulfonamide;
N-(4-(4-oxo-7-(phenylethynyl)-4H-chromen-3-yl)phenyl)methanesulfonamide;
N-(4-(7-(cyclopropylethynyl)-4-oxo-4H-chromen-3-yl)phenyl)methanesulfonamide;
N-(4-(7-(((1S,2R)-2-hydroxycyclopentyl)ethynyl)-4-oxo-4H-chromen-3-yl)phenyl)methanesulfonamide;
N-(4-(7-(3-methoxyprop-1-ynyl)-4-oxo-4H-chromen-3-yl)phenyl)cyclopropanesulfonamide;
tert-butyl 4-((3-(4-(methylsulfonamido)phenyl)-4-oxo-4H-chromen-7-yl)ethynyl)piperidine-1-carboxylate;
tert-butyl 3-((3-(4-(methylsulfonamido)phenyl)-4-oxo-4H-chromen-7-yl)ethynyl)azetidine-1-carboxylate;
N-(4-(4-oxo-7-((2-oxo-1,2-dihydropyridin-4-yl)ethynyl)-4H-chromen-3-yl)phenyl)methanesulfonamide;
N-(4-(7-((1-(cyclopropanecarbonyl)azetidin-3-yl)ethynyl)-4-oxo-4H-chromen-3-yl)phenyl)methanesulfonamide;
N-(4-(4-oxo-7-(piperidin-4-ylethynyl)-4H-chromen-3-yl)phenyl)methanesulfonamide;
N-(4-(7-((1-(cyclopropanecarbonyl)piperidin-4-yl)ethynyl)-4-oxo-4H-chromen-3-yl)phenyl)methanesulfonamide;
N-(4-(7-((1,2-dimethyl-1H-imidazol-5-yl)ethynyl)-4-oxo-4H-chromen-3-yl)phenyl)methanesulfonamide;
N-(4-(7-((1-isopropyl-1H-imidazol-5-yl)ethynyl)-4-oxo-4H-chromen-3-yl)phenyl)methanesulfonamide;
N-(4-(7-((1-methyl-1H-imidazol-4-yl)ethynyl)-4-oxo-4H-chromen-3-yl)phenyl)methanesulfonamide;
N-(4-(7-(azetidin-3-ylethynyl)-4-oxo-4H-chromen-3-yl)phenyl)methanesulfonamide;
cyclopentyl 3-((3-(4-(methyl sulfonamido)phenyl)-4-oxo-4H-chromen-7-yl)ethynyl)azetidine-1-carboxylate;
N-(4-(4-oxo-7-((tetrahydro-2H-pyran-4-yl)ethynyl)-4H-chromen-3-yl)phenyl)methanesulfonamide;
N-(4-(7-((1-isobutylazetidin-3-yl)ethynyl)-4-oxo-4H-chromen-3-yl)phenyl)methanesulfonamide;
N-(4-(7-((1-(3-methoxypropanoyl)azetidin-3-yl)ethynyl)-4-oxo-4H-chromen-3-yl)phenyl)methanesulfonamide;
N-(4-(7-((1-(3,3-difluorocyclobutanecarbonyl)-azetidin-3-yl)ethynyl)-4-oxo-4H-chromen-3-yl)phenyl)methanesulfonamide;
N-(4-(7-((1-(3-(dimethylamino)propanoyl)-azetidin-3-yl)ethynyl)-4-oxo-4H-chromen-3-yl)phenyl)methanesulfonamide;
N-(4-(7-((1-(2-hydroxyacetyl)azetidin-3-yl)ethynyl)-4-oxo-4H-chromen-3-yl)phenyl)methanesulfonamide;
N-(4-(7-((1-(3-hydroxy-3-methylcyclobutane-carbonyl)azetidin-3-yl)ethynyl)-4-oxo-4H-chromen-3-yl)phenyl)methanesulfonamide;
N-(4-(7-((1-(2-hydroxy-2-methylpropanoyl)-azetidin-3-yl)ethynyl)-4-oxo-4H-chromen-3-yl)phenyl)methanesulfonamide;
N-(4-(7-((1-(3-methyloxetane-3-carbonyl)azetidin-3-yl)ethynyl)-4-oxo-4H-chromen-3-yl)phenyl)methanesulfonamide;
N-(4-(7-((1-(2-hydroxypropanoyl)azetidin-3-yl)ethynyl)-4-oxo-4H-chromen-3-yl)phenyl)methanesulfonamide;
N-(4-(7-((1-(1-methylpiperidine-4-carbonyl)azetidin-3-yl)ethynyl)-4-oxo-4H-chromen-3-yl)phenyl)methanesulfonamide;
N-(4-(7-((1-(2,2-difluorocyclopropane-carbonyl)azetidin-3-yl)ethynyl)-4-oxo-4H-chromen-3-yl)phenyl)methanesulfonamide;
N-(4-(7-((1-(cyclobutanecarbonyl)azetidin-3-yl)ethynyl)-4-oxo-4H-chromen-3-yl)phenyl)methanesulfonamide;

N-(4-(7-((1-(1-methylcyclopropanecarbonyl)-azetidin-3-yl)ethynyl)-4-oxo-4H-chromen-3-yl)phenyl)methanesulfonamide;

tert-butyl 1-(3-((3-(4-(methylsulfonamido)-phenyl)-4-oxo-4H-chromen-7-yl)ethynyl)azetidine-1-carbonyl)-cyclobutylcarbamate;

tert-butyl 1-(3-((3-(4-(methylsulfonamido)phenyl)-4-oxo-4H-chromen-7-yl)ethynyl)azetidine-1-carbonyl)cyclopropylcarbamate;

tert-butyl (1-(3-((3-(4-(methylsulfonamido)-phenyl)-4-oxo-4H-chromen-7-yl)ethynyl)azetidine-1-carbonyl)cyclopropyl)-methylcarbamate;

N-(4-(4-oxo-7-(pyridin-3-ylethynyl)-4H-chromen-3-yl)phenyl)methanesulfonamide;

N-(4-(4-oxo-7-(pyrimidin-5-ylethynyl)-4H-chromen-3-yl)phenyl)methanesulfonamide;

N-(4-(7-((1-hydroxycyclopentyl)ethynyl)-4-oxo-4H-chromen-3-yl)phenyl)methanesulfonamide;

N-(4-(4-oxo-7-(pyridin-2-ylethynyl)-4H-chromen-3-yl)phenyl)methanesulfonamide;

N-(4-(7-((1-aminocyclohexyl)ethynyl)-4-oxo-4H-chromen-3-yl)phenyl)methanesulfonamide;

N-(4-(7-((1-hydroxycyclohexyl)ethynyl)-4-oxo-4H-chromen-3-yl)phenyl)methanesulfonamide;

N-(4-(7-(3-methoxyprop-1-ynyl)-4-oxo-4H-chromen-3-yl)phenyl)methanesulfonamide; and N-(4-(7-((1-methyl-1H-imidazol-5-yl)ethynyl)-4-oxo-4H-chromen-3-yl)phenyl)methanesulfonamide; or a pharmaceutically acceptable salt thereof.

DETAILED DESCRIPTION OF THE INVENTION

Detailed Description

Before the present compositions and methods are described, it is to be understood that the disclosure is not limited to the particular compounds, compositions, methodologies, protocols, cell lines, assays, and reagents described, as these may vary. It is also to be understood that the terminology used herein is intended to describe particular embodiments, and is in no way intended to limit the scope as set forth in the appended claims.

DETAILED DESCRIPTION OF FIGURES

FIG. 1 is a graphical representation of cocaine cue replacement study design.

Figure 2:
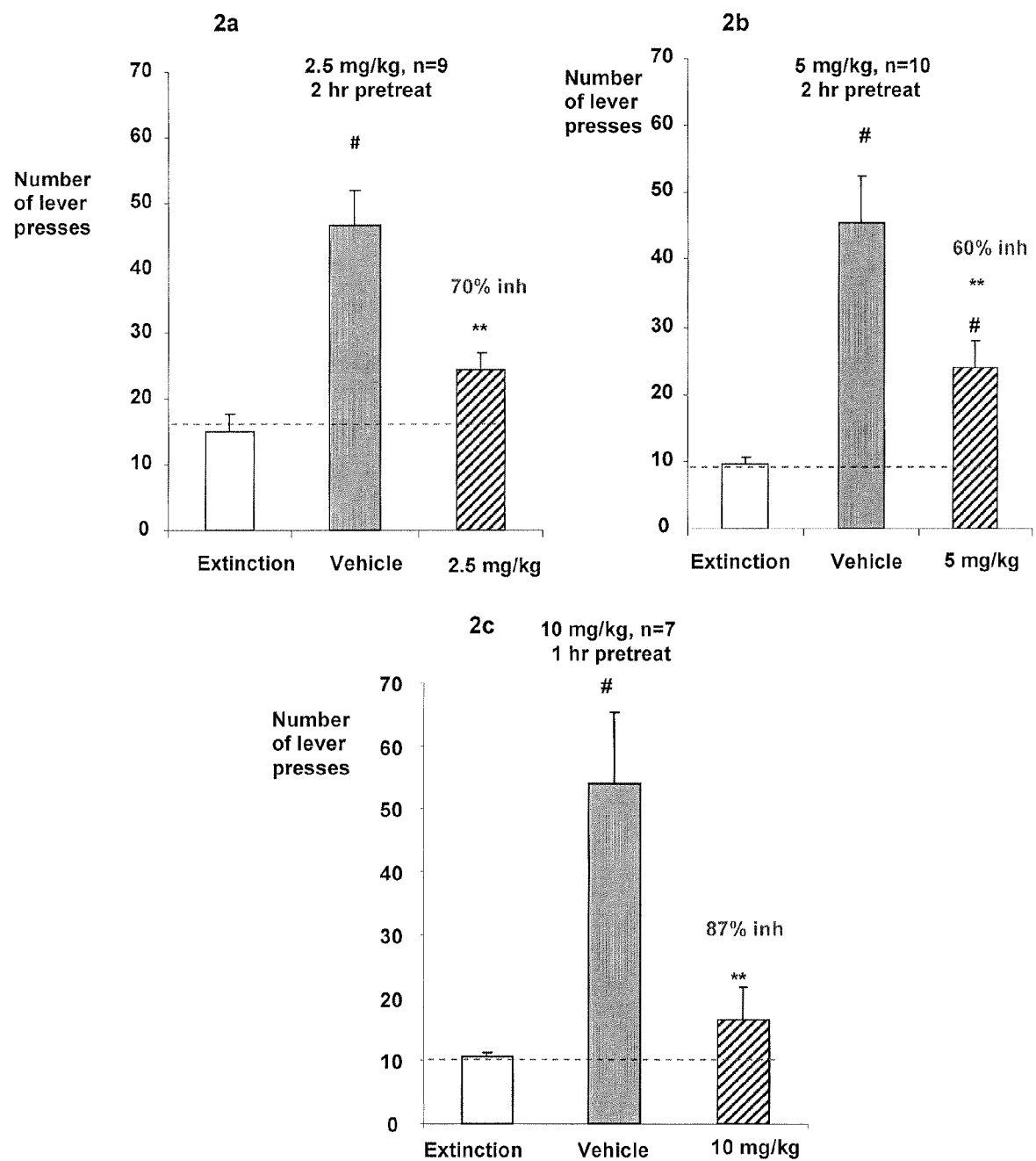

FIGS. 2A, 2B, and 2C collectively show significant inhibition of cocaine cue reinstatement in rats orally administered a compound of the invention compared to vehicle.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, or 8 carbon atoms. This term is exemplified by groups such as methyl, ethyl, n-propyl, iso-propyl, n-butyl, iso-butyl, t-butyl, n-hexyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-4 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-4 atoms as defined above.

The term "lower alkyl" refers to a monoradical branched or unbranched saturated hydrocarbon chain having 1, 2, 3, or 4 carbon atoms. This term is exemplified by groups such as methyl, ethyl, n-propyl, iso-propyl, n-butyl and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, or 2 atoms as defined for substituted alkyl, or a lower alkyl group as defined above that has both 1, or 2 substituents as defined above and is also interrupted by 1, or 2 atoms as defined above.

The term "alkylene" refers to a diradical of a branched or unbranched saturated hydrocarbon chain, having 1, 2, 3, 4, 5, 6, 7, or 8 carbon atoms, preferably 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1-8 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy and the like.

The term "lower alkoxy" refers to the group R—O—, where R is optionally substituted alkyl as defined above.

The term "alkylthio" refers to the group R—S—, where R is as defined for alkoxy.

The term "alkenyl" refers to a monoradical of a branched or unbranched unsaturated hydrocarbon group having from 2 to 8 carbon atoms, preferably 2 to 6 carbon atoms and even more preferably 2 to 4 carbon atoms and having 1-2, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 4 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 8 carbon atoms, more preferably 2 to 6 carbon atoms and even more preferably 2 to 4 carbon atoms and having at least 1 and preferably from 1-2 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxyl, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 10 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group Ar—S—, where Ar is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents independently chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl or —C(O)β-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted alkoxy, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, or 12 carbon atoms and 1, 2, 3 or 4 heteroatoms independently selected from oxygen, nitrogen and sulfur within at least one ring. Such heteroaryl groups can have a single ring (e.g., pyridyl or fury') or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, thiazole, isothiazole, phenazine, oxazole, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives. Unless otherwise constrained by the definition for the heteroaryl or heteroarylene substituent, such heteroaryl or hetarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents independently chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 10 carbon atoms and from 1 to 5 hetero atoms, preferably 1, 2, or 3 heteroatoms, independently selected from nitrogen, sulfur, phosphorus, and/or oxygen within the ring. Heterocyclic groups can have a single ring or multiple condensed rings, and include tetrahydrofuranyl, morpholino, oxathiane, thiomorpholino, tetraydropthiophenyl, tetrahydropyranyl, tetrahydrothiopyranyl, piperidinyl, triazolidino, piperazinyl, dihydropyridino, pyrrolidinyl, imidazolidino, hexahydropyrimidine, hexahydropyridazine, imidazoline, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, carboxycycloalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—.

The term "thiocarbonyl" refers to a group —C(S)—.

The term "carboxyl" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means.

The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated. "Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

"Parenteral administration" is the systemic delivery of the therapeutic agent via injection to the patient.

The term "patients" refers to humans.

The term "therapeutically effective amount" refers to that amount of a compound of Formula I that is sufficient to effect treatment, as defined below, when administered to a patient in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means administration of a compound of the invention to a patient having a disease or susceptible to a disease for purposes including:
  (i) preventing the disease, that is, causing the clinical symptoms of the disease not to develop;
  (ii) inhibiting the disease, that is, arresting the development of clinical symptoms; and/or
  (iii) relieving the disease, that is, alleviating the symptoms of the diseases or causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, diethyl amine, tri(iso-propyl) amine, tri(n-propyl) amine, ethanolamine, 2-dimethylaminoethanol, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is propan-2-ol, $R^2$ is methyl, and $R^3$ is hydrogen:

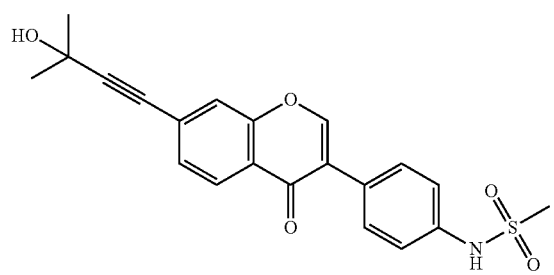 [SMILES: CC(C)(O)C#Cc1ccc2c(=O)c(-c3ccc(NS(C)(=O)=O)cc3)coc2c1]

namely: N-(4-(7-(3-hydroxy-3-methylbut-1-ynyl)-4-oxo-4H-chromen-3-yl)phenyl)methanesulfonamide Synthetic Reaction Parameters The terms "solvent", "inert organic solvent" or "inert solvent" mean a solvent inert under the conditions of the reaction being described in conjunction therewith. Examples include, for example, benzene, toluene, acetonitrile, tetrahydrofuran ("THF"), dimethylformamide ("DMF"), chloroform, methylene chloride (or dichloromethane), diethyl ether, methanol, pyridine and the like. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I in which X, Y and Z are all —$CR^4$—, in which $R^4$ is hydrogen may be prepared as shown in Reaction Scheme I.

REACTION SCHEME I

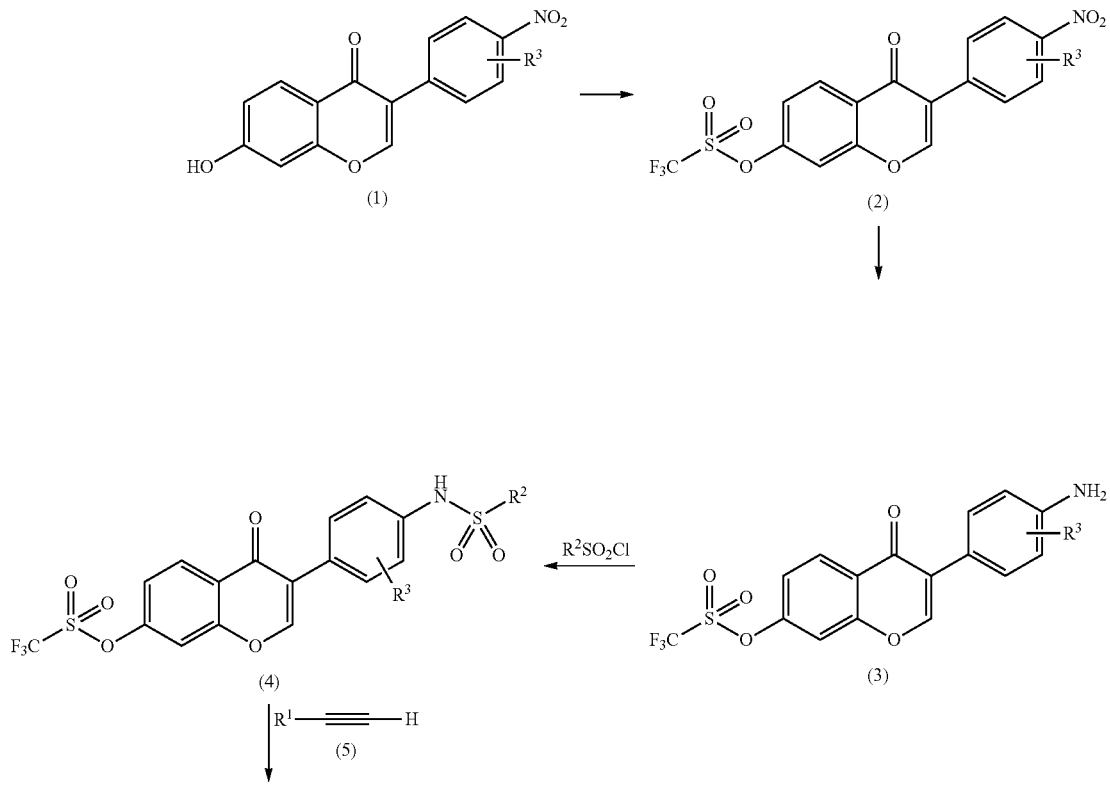

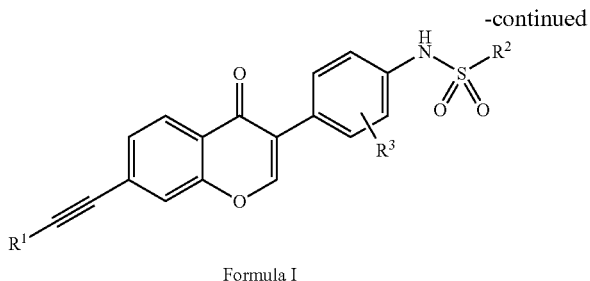

Formula I

Step 1—Preparation of a Compound of Formula (2)

The compound of formula (1) is commercially available, or is prepared by means well known in the art. In general, the compound of formula (1) is dissolved in an inert solvent, for example dichloromethane, at a temperature of about 0° C., and a tertiary base, for example pyridine, is added, followed by triflic anhydride. The mixture is allowed to warm to room temperature, and stirred until the reaction is complete, generally about 1 hour. When the reaction is substantially complete, the product of formula (2) is isolated by conventional means.

Step 2—Preparation of a Compound of Formula (3)

To a suspension of the compound of formula (2) in an inert solvent, for example tetrahydrofuran, is added a freshly prepared solution of sodium dithionite in water. The mixture is stirred at room temperature for about 2 hours and then additional sodium dithionite added. The reaction mixture is stirred until the reaction is complete, typically about 24 hours at room temperature. When the reaction is substantially complete, the product of formula (3) is isolated by conventional means, and optionally used in the next reaction without further purification Step 3—Preparation of a Compound of Formula (4)

To a suspension of the compound of formula (3) in a tertiary base, for example pyridine at about 0° C., methanesulfonyl chloride is slowly added and the mixture allowed to warm to about room temperature. When the reaction is complete, typically about 2 hours, water is added in portions under vigorous stirring. When the reaction is substantially complete, the crude product of formula (4) is isolated by conventional means, and purified conventionally, for example by heating in an inert solvent, for example acetonitrile, cooling, and filtering off the product of formula (4).

Step 4—Preparation of a Compound of Formula I

In general, the compound of formula (4) is dissolved in an inert solvent at room temperature, for example tetrahydrofuran, and the substituted alkyne of formula (5) is added, along with PdCl$_2$(PPh$_3$)$_2$, copper iodide, triphenylphosphine, and an organic base, for example triethylamine. The mixture is heated in a microwave for about 10-60 minutes at about 60-100° C. When the reaction is substantially complete, the product of Formula I is isolated and purified by conventional means.

An alternative method for preparing compounds of Formula I is shown in Reaction Scheme II.

REACTION SCHEME II

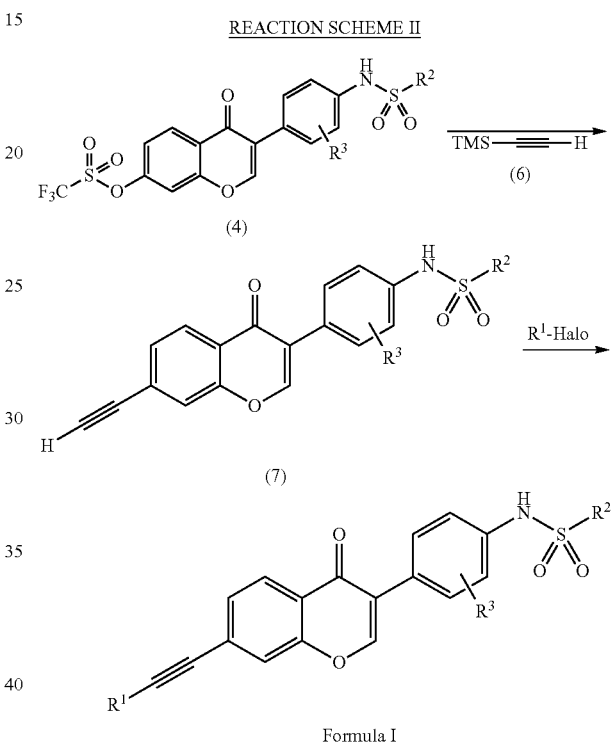

Formula I

Step 1—Preparation of a Compound of Formula (7)

The compound of formula (4) (for example prepared as shown in Reaction Scheme I) in an inert solvent, for example tetrahydrofuran, is contacted with trimethylsilylacetylene, PdCl$_2$(PPh$_3$)$_2$, copper iodide, triphenylphosphine, and a tertiary amine, for example triethylamine (3.12 ml, 4.0 eq). The mixture is heated in a microwave for about 30 minutes at about 85° C. When the reaction is substantially complete, the product is isolated and purified by conventional means.

The product is then dissolved in an inert solvent, or mixture of inert solvents, for example a mixture of methanol/tetrahydrofuran, and a mild base, for example is added, and the mixture stirred at about room temperature for about 1 hour. When the reaction is substantially complete, the product of Formula (7) is isolated and purified by conventional means.

Step 3—Preparation of a Compound of Formula (I)

The compound of formula (7) is combined with an appropriate compound of the formula R1-halo, for example 4-bromo-2-tert-butoxypyridine. PdCl$_2$(PPh$_3$)$_2$, copper iodide, triphenylphosphine, and a tertiary base, for example triethylamine in an inert solvent, for example tetrahydrofuran are heated in microwave for about 30 minutes at about 85° C. When the reaction is substantially complete, the product is isolated and purified by conventional means, then deprotected by treatment with an acid, for example trifluoroacetic acid in an inert solvent, for example dichloromethane, for about 1 hour at room temperature, and the product of Formula (I) is isolated conventionally.

Utility, Testing and Administration

General Utility

The compounds of Formula I are generally effective in the treatment of conditions that respond to administration of ALDH-2 inhibitors. Specifically, the compounds of Formula I are useful in the treatment of addiction to dopamine-producing agents of addiction such as, for example, cocaine, opiates, amphetamines, nicotine, excessive food intake (over eating) and alcohol.

While not wishing to be bound by theory, it is believed that ALDH-2 inhibitors are effective in treating addiction as a consequence of their ability to normalize the increased dopamine levels associated with various addictive behaviors. See, N. D. Volkow et al., Dopamine in drug abuse and addiction: results from imaging studies and treatment implications, *Mol. Psychiatry*. 9 (2004), pp. 557-569; and B. J. Everitt and M. E. Wolf, Psychomotor stimulant addiction: a neural systems perspective, *J. Neurosci*. 22 (2002), pp. 3312-3320.

Given this proposed mechanism of action, ALDH-2 inhibitors such as the compounds of Formula I are useful in the treatment of addictive and compulsive behaviors and neurological conditions associated with increased dopamine levels. Such behaviors and conditions include, but are not limited to, compulsive gambling, over eating, shopping, obsessive compulsive disorder (OCD), schizophrenia, attention deficit hyperactivity disorder, and the like.

Testing

Activity testing is conducted as described in those patents and patent applications referenced above, and in the Examples below, and by methods apparent to one skilled in the art. For example, as described in "The Mitrochondrial Monoamine Oxidase-Aldehyde Dehydrogenase Pathway: A Potential Site of Action of Daidzin", J. Med. Chem. 2000, 43, 4169-4179. In general, the compounds of Formula I are assayed to determine their effects on MAO and ALDH-2 independently using the membrane and lysate of a density-gradient-purified mitochondria preparation as the respective enzyme sources. The results are expressed in $IC_{50}$ values.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for patients, each unit containing a predetermined quantity of active material calculated to produce the desired therapeutic effect, in association with a suitable pharmaceutical excipient (e.g., a tablet, capsule, or ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) in which $R^3$ is Hydrogen

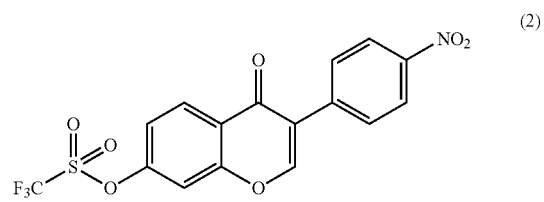 [SMILES: O=c1c(-c2ccc([N+](=O)[O-])cc2)coc2cc(OS(=O)(=O)C(F)(F)F)ccc12]

To a suspension of 7-hydroxy-3-(4-nitrophenyl)-4H-chromen-4-one (commercially available, (10 g, 48.3 mmol) in dichloromethane (100 mL), pyridine (15.6 mL, 193.2 mmol) was added and the mixture was then cooled in an ice-bath. To this solution at 0° C., triflic anhydride (16.3 mL, 96.6 mmol) was added slowly and then the solution was warmed up to room temperature and stirred for 1 hour until the reaction was completed. The reaction mixture was partitioned between ethyl acetate and water. The organic phase was dried with magnesium sulfate and solvent removed under reduced pressure. The residue was heated in acetonitrile and the solids filtered off, to give 3-(4-nitrophenyl)-4-oxo-4H-chromen-7-yl trifluoromethanesulfonate.

EXAMPLE 2

Preparation of a Compound of Formula (3)

A. Preparation of a Compound of Formula (3) in which $R^3$ is Hydrogen

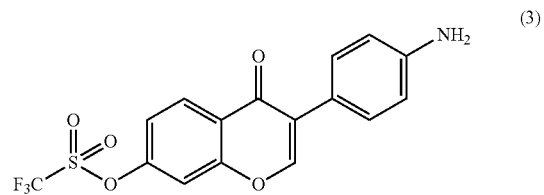

To a suspension of 3-(4-nitrophenyl)-4-oxo-4H-chromen-7-yl trifluoromethanesulfonate (5.0 g, 14.75 mmol) in tetrahydrofuran (20 mL) was added a freshly prepared solution of sodium dithionite (5.13 g in 20 mL). The mixture was stirred at room temperature for 2 hours and then additional sodium dithionite (2.57 g) was added in two portions. The reaction mixture was stirred for 24 hours at room temperature, after which time the reaction was complete. The organic solvent was evaporated under reduced pressure and then water (10 mL) was added to the suspension. The solids in suspension were filtered off and dried under high vacuum. The product was heated with acetonitrile and stirred until room temperature was achieved. The solids were filtered off to provide 3-(4-aminophenyl)-4-oxo-4H-chromen-7-yl trifluoromethanesulfonate (4.1 g), which was used in the next step without further purification.

EXAMPLE 3

Preparation of a Compound of Formula (4)

A. Preparation of a Compound of Formula (4) in which $R^2$ is Methyl and $R^3$ is Hydrogen

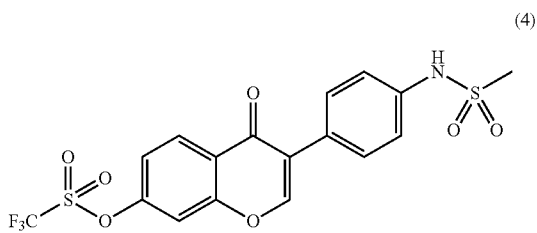 [SMILES: CS(=O)(=O)Nc1ccc(-c2coc3cc(OS(=O)(=O)C(F)(F)F)ccc3c2=O)cc1]

(4)

To a suspension of 3-(4-aminophenyl)-4-oxo-4H-chromen-7-yl trifluoromethanesulfonate (2.2 g, 7.12 mmol) in pyridine (10 mL) at 0° C. was added methanesulfonyl chloride (1.1 mL, 14.24 mmol) over 5 minutes, and then warmed up to room temperature under stirring conditions. After 2 hours the reaction was complete, and water was added in portions under vigorous stirring. The organic phase was then separated and concentrated and the resulting solids were filtered and dried under high vacuum. The solids were heated in acetonitrile, stirred until room temperature was achieved, then filtered off to give 3-(4-(methylsulfonamido)phenyl)-4-oxo-4H-chromen-7-yl trifluoromethanesulfonate (2.49 g). $^1$H NMR (DMSO, 400 MHz) δ 9.87 (s, 1H); 8.60 (s, 1H); 8.31 (d, J=8.0 Hz, 1H); 8.09 (s, 1H); 7.65 (d, J=8.0 Hz, 1H); 7.57 (d, J=8.4 Hz, 2H); 7.27 (d, J=8.4 Hz, 2H); 3.01 (s, 3 H).

EXAMPLE 4

Preparation of a Compound of Formula I

A. Preparation of a Compound of Formula I in which $R^1$ is 2-Methylpropan-2-ol, $R^2$ is Methyl, and $R^3$ is Hydrogen

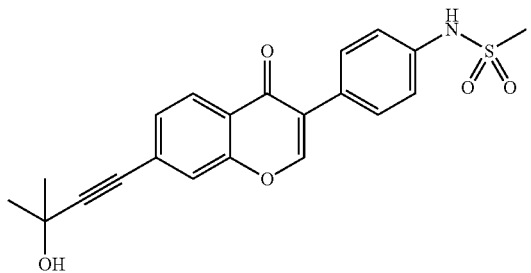 [SMILES: CC(C)(O)C#Cc1ccc2c(=O)c(-c3ccc(NS(C)(=O)=O)cc3)coc2c1]

3-(4-(methylsulfonamido)phenyl)-4-oxo-4H-chromen-7-yltrifluoromethanesulfonate (2.0 g, 4.32 mmol), 2-methylbut-3-yn-2-ol (0.48 ml, 1.2 eq), PdCl$_2$(PPh$_3$)$_2$ (140 mg, 0.05 eq), copper iodide (23 mg 0.002 eq), triphenylphosphine (32 mg 0.03 eq) and triethylamine (2.5 ml, 4.0 eq) were combined in dry tetrahydrofuran (10 ml), and the mixture heated in a microwave for 30 minutes at 85° C. The reaction mixture was partitioned between ethyl acetate and water, the organic phase dried over magnesium sulfate, and the solvent removed under reduced pressure. The crude product was heated in acetonitrile, cooled, and the solids filtered off. This procedure was repeated twice in order to afford N-(4-(7-(3-hydroxy-3-methylbut-1-ynyl)-4-oxo-4H-chromen-3-yl)-phenyl)methanesulfonamide.

MS found for C$_{21}$H$_{19}$NO$_5$S as (M+H)$^+$ 398.06 $^1$H NMR (400 MHz, dmso-d$_6$): δ: 9.85 (s, 1H), 8.53 (s, 1H), 8.08 (d, J=8.0 Hz, 1H), 7.69 (s, 1H), 7.55 (d, J=8.0 Hz, 2H), 7.46 (d, J=8.0 Hz, 1H), 7.25 (d, J=8.0 Hz, 2H), 5.59 (s, 1H), 3.01 (s, 3H), 1.48 (s, 6H).

B. Preparation of Other Compounds of Formula I

Similarly, following the procedure of Example 4A, but optionally replacing 3-(4-(methylsulfonamido)phenyl)-4-oxo-4H-chromen-7-yltrifluoromethanesulfonate with other compounds of formula (4), and optionally replacing 2-methylbut-3-yn-2-ol with other alkynes of formula (5), the following compounds of Formula I were prepared:

N-(4-(7-(3-methoxyprop-1-ynyl)-4-oxo-4H-chromen-3-yl)phenyl)methanesulfonamide

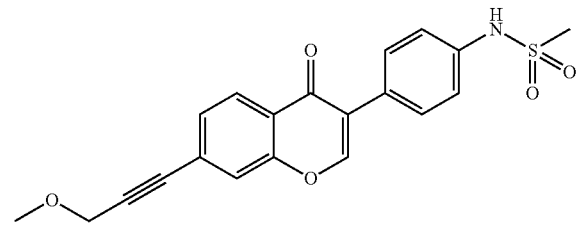 [SMILES: COCC#Cc1ccc2c(=O)c(-c3ccc(NS(C)(=O)=O)cc3)coc2c1]

MS found for C$_{20}$H$_{17}$NO$_5$S as (M+H)$^+$ 384.08 $^1$H NMR (400 MHz, dmso-d$_6$): $^1$H-NMR (DMSO) δ: 9.92 (s, 1H), 8.55 (s, 1H), 8.11 (d, J=8.8 Hz, 1H), 7.61 (s, 1H), 7.61-7.55 (m, 3H), 7.25 (d, J=6.4 Hz, 2H), 4.39 (s, 2H), 3.35 (s, 3H), 3.00 (s, 3H).

N-(4-(7-((1-hydroxycyclopentyl)ethynyl)-4-oxo-4H-chromen-3-yl)phenyl)methanesulfonamide

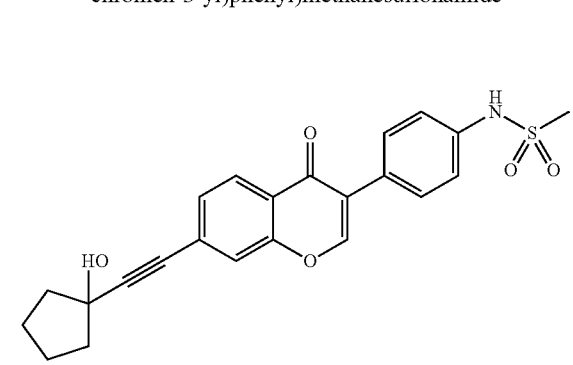

MS found for C$_{23}$H$_{21}$NO$_5$S as (M+H)$^+$ 424.16 $^1$H NMR (400 MHz, dmso-d$_6$): $^1$H-NMR (DMSO) δ: 9.85 (s, 1H), 8.53

(s, 1H), 8.09 (s, 1H), 7.70 (s, 1H), 7.55 (s, 2H), 7.47 (s, 1H), 7.26 (s, 2H), 5.45 (s, 1H), 3.01 (s, 3H), 1.93-1.70 (m, 8H).

N-(4-(4-oxo-7-(pyridin-2-ylethynyl)-4H-chromen-3-yl)phenyl)methanesulfonamide

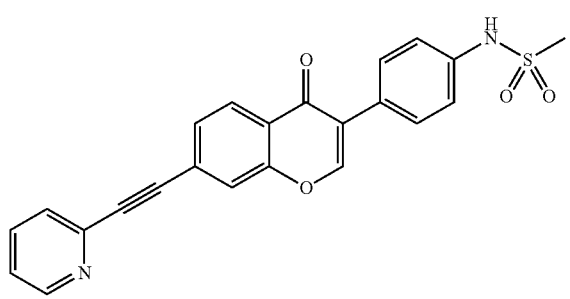 [SMILES: CS(=O)(=O)Nc1ccc(-c2coc3cc(C#Cc4ccccn4)ccc3c2=O)cc1]

MS found for $C_{23}H_{16}N_2O_4S$ as $(M+H)^+$ 417.12 $^1$H NMR (400 MHz, dmso-d$_6$): $^1$H-NMR (DMSO) δ: 9.86 (s, 1H), 8.65 (s, 1H), 8.57 (s, 1H), 8.17 (d, J=6.8 Hz, 1H), 7.98-7.89 (m, 2H), 7.73-7.46 (m, 5H), 7.27-7.26 (m, 2H), 3.01 (s, 3H).

N-(4-(7-((1-aminocyclohexyl)ethynyl)-4-oxo-4H-chromen-3-yl)phenyl)methanesulfonamide

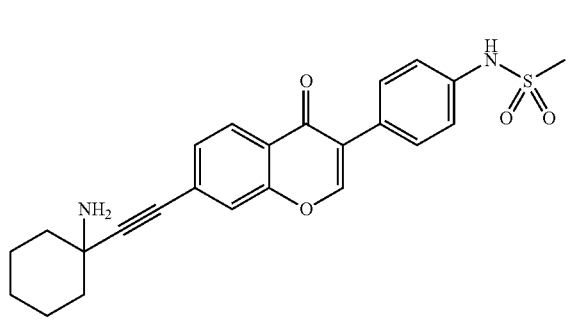 [SMILES: CS(=O)(=O)Nc1ccc(-c2coc3cc(C#CC4(N)CCCCC4)ccc3c2=O)cc1]

MS found for $C_{24}H_{24}N_2O_4S$ as $(M+H)^+$ 437.20 $^1$H NMR (400 MHz, dmso-d$_6$): $^1$H-NMR (DMSO) δ: 8.52 (s, 1H), 8.07 (d, J=8.8 Hz, 1H), 7.65 (s, 1H), 7.54-7.24 (m, 5H), 2.99 (s, 3H), 1.80-1.18 (m, 10H). N-(4-(7-((1-hydroxycyclohexyl)ethynyl)-4-oxo-4H-chromen-3-yl)phenyl)methanesulfonamide;

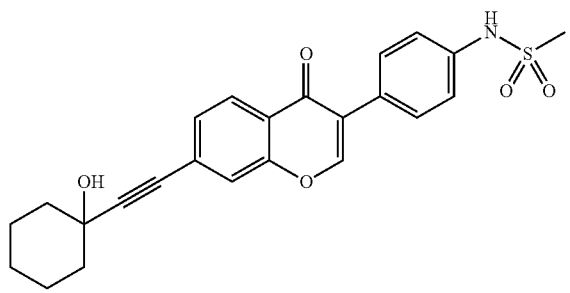 [SMILES: CS(=O)(=O)Nc1ccc(-c2coc3cc(C#CC4(O)CCCCC4)ccc3c2=O)cc1]

MS found for $C_{24}H_{23}NO_5S$ as $(M+H)^+$ 438.22 $^1$H NMR (400 MHz, dmso-d$_6$): $^1$H-NMR (DMSO) δ: 9.87 (s, 1H), 8.53

(s, 1H), 8.09 (d, J=8.4 Hz, 1H), 7.71 (s, 1H), 7.56-7.47 (m, 3H), 7.24 (d, J=8.4 Hz, 2H), 5.56 (s, 1H), 3.00 (s, 3H), 1.87-1.25 (m, 10H).

N-(4-(4-oxo-7-(pyrimidin-5-ylethynyl)-4H-chromen-3-yl)phenyl)methanesulfonamide

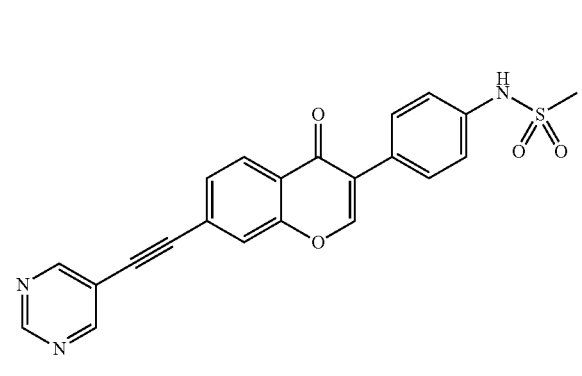 [SMILES: CS(=O)(=O)Nc1ccc(-c2coc3cc(C#Cc4cncnc4)ccc3c2=O)cc1]

MS found for $C_{22}H_{15}N_3O_4S$ as $(M+H)^+$ 418-12 $^1$H NMR (400 MHz, dmso-d$_6$): $^1$H-NMR (DMSO) δ: 9.85 (s, 1H), 9.23 (s, 1H), 9.07 (s, 2H), 8.56 (s, 1H), 8.17 (d, J=8.0 Hz, 1H), 7.97 (s, 1H), 7.69-7.66 (m, 1H), 7.55 (d, J=8.4 Hz, 2H), 7.25 (d, J=8.4 Hz, 2H), 3.00 (s, 3H).

N-(4-(4-oxo-7-(pyridin-3-ylethynyl)-4H-chromen-3-yl)phenyl)methanesulfonamide

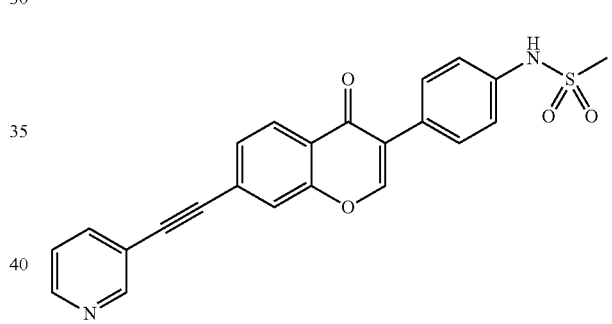

MS found for $C_{23}H_{16}N_2O_4S$ as $(M+H)^+$ 417.15 $^1$H NMR (400 MHz, dmso-d$_6$): $^1$H-NMR (DMSO) δ: 9.86 (s, 1H), 8.84 (s, 1H), 8.64 (d, J=4.4 Hz, 1H), 8.56 (s, 1H), 8.15 (s, 1H), 8.08 (s, 1H), 7.95 (s, 1H), 7.66 (d, J=9.6 Hz, 1H), 7.56-7.54 (m, 3H), 7.25 (d, J=8.8 Hz, 2H), 3.00 (s, 3H).

N-(4-(7-(((1S,2R)-2-hydroxycyclopentyl)ethynyl)-4-oxo-4H-chromen-3-yl)phenyl)methanesulfonamide

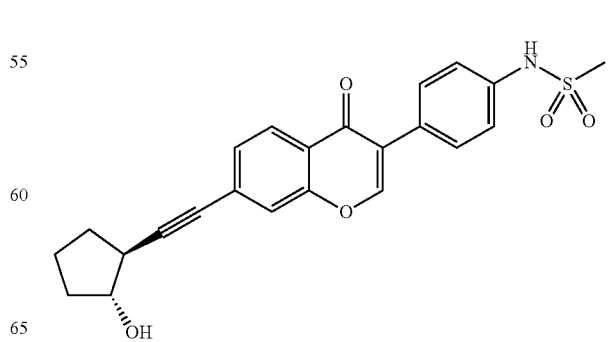

MS found for $C_{23}H_{21}NO_5S$ as $(M+H)^+$ 424.16 $^1$H NMR (400 MHz, dmso-$d_6$): $^1$H-NMR (DMSO) δ: 9.83 (s, 1H), 8.50 (s, 1H), 8.04 (d, J=8.4 Hz, 1H), 7.66 (d, J=1.2 Hz, 1H), 7.54 (d, J=8.4 Hz, 2H), 7.44-7.42 (m, 1H), 7.23 (d, J=8.8 Hz, 2H), 5.05 (d, J=4.8 Hz, 1H), 4.11-4.08 (m, 1H), 2.99 (s, 3H), 2.99-2.72 (m, 1H), 2.08-2.07 (m, 1H), 1.91-1.86 (m, 1H), 1.69-1.64 (m, 2H), 1.51-1.46 (m, 1H).

N-(4-(7-(cyclopropylethynyl)-4-oxo-4H-chromen-3-yl)phenyl)methanesulfonamide

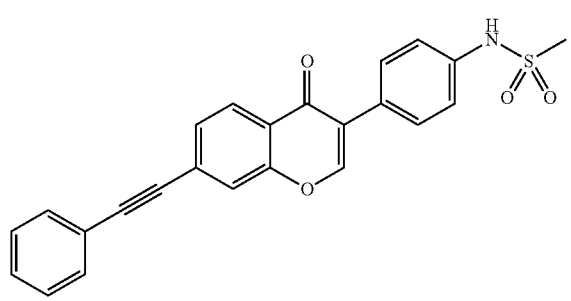 [SMILES: CS(=O)(=O)Nc1ccc(-c2coc3cc(C#Cc4ccccc4)ccc3c2=O)cc1]

MS found for $C_{21}H_{17}NO_4S$ as $(M+H)^+$ 380.06 $^1$H NMR (400 MHz, dmso-$d_6$): $^1$H-NMR (DMSO) δ: 9.84 (s, 1H), 8.51 (s, 1H), 8.04 (d, J=8.0 Hz, 1H), 7.67 (s, 1H), 7.55 (d, J=8.4 Hz, 1H), 7.43 (d, J=8.0 Hz, 2H), 7.25 (d, J=8.4 Hz, 2H), 3.00 (s, 3H), 1.63-1.59 (m, 1H), 0.96-0.92 (m, 2H), 0.83-0.78 (m, 2H).

N-(4-(4-oxo-7-(phenylethynyl)-4H-chromen-3-yl)phenyl)methanesulfonamide

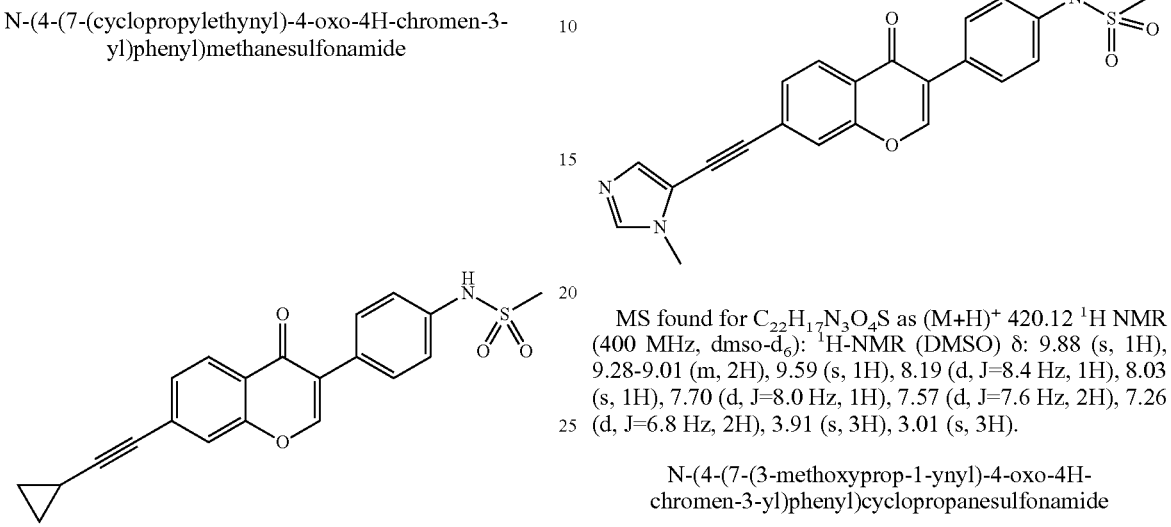

MS found for $C_{24}H_{17}NO_4S$ as $(M+H)^+$ 416.07 $^1$H NMR (400 MHz, dmso-$d_6$): $^1$H-NMR (DMSO) δ: 9.86 (s, 1H), 8.56 (s, 1H), 8.14 (d, J=8.4 Hz, 1H), 7.91 (s, 1H), 7.65-7.46 (m, 8H), 7.26 (d, J=8.4 Hz, 1H), 3.01 (s, 3H).

N-(4-(7-((1-methyl-1H-imidazol-5-yl)ethynyl)-4-oxo-4H-chromen-3-yl)phenyl)methanesulfonamide

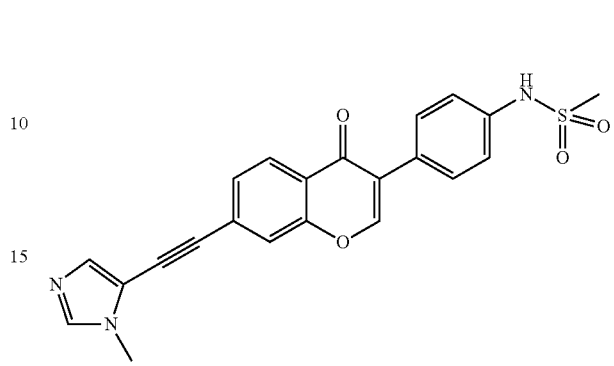

MS found for $C_{22}H_{17}N_3O_4S$ as $(M+H)^+$ 420.12 $^1$H NMR (400 MHz, dmso-$d_6$): $^1$H-NMR (DMSO) δ: 9.88 (s, 1H), 9.28-9.01 (m, 2H), 9.59 (s, 1H), 8.19 (d, J=8.4 Hz, 1H), 8.03 (s, 1H), 7.70 (d, J=8.0 Hz, 1H), 7.57 (d, J=7.6 Hz, 2H), 7.26 (d, J=6.8 Hz, 2H), 3.91 (s, 3H), 3.01 (s, 3H).

N-(4-(7-(3-methoxyprop-1-ynyl)-4-oxo-4H-chromen-3-yl)phenyl)cyclopropanesulfonamide

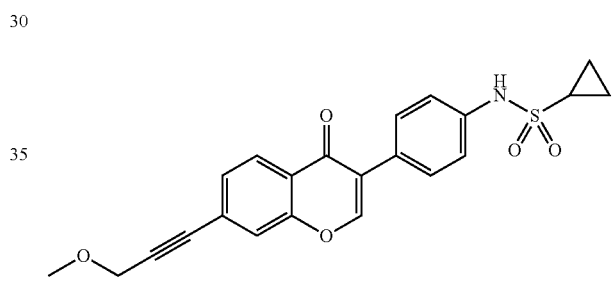

MS found for $C_{22}H_{19}NO_5S$ as $(M+H)^+$ 410.15 $^1$H NMR (400 MHz, dmso-$d_6$): $^1$H-NMR (DMSO) δ: 9.82 (s, 1H), 8.53 (s, 1H), 8.08 (d, J=8.0 Hz, 1H), 7.8 (s, 1H), 7.55-7.51 (m, 2H), 7.41 (d, J=5.2 Hz, 1H), 7.27 (d, J=8.8 Hz, 2H), 4.37 (s, 2H), 3.34 (s, 3H), 2.7-2.62 (m, 1H), 0.94-0.91 (m, 4H).

tert-butyl 4-((3-(4-(methylsulfonamido)phenyl)-4-oxo-4H-chromen-7-yl)ethynyl)piperidine-1-carboxylate

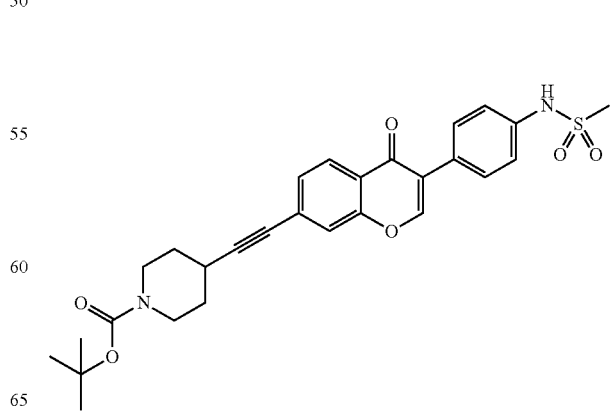

MS found for $C_{28}H_{30}N_2O_6S$ as $(M+H)^+$ 523.01 $^1H$ NMR (400 MHz, dmso-$d_6$): δ: 9.86 (s, 1H); 8.58 (s, 1H); 8.09 (d, J=8.4 Hz, 1H); 7.74 (s, 1H); 7.57-7.48 (m, 3H); 7.27 (d, J=8.4 Hz, 2H), 3.68-3.36 (m, 2H); 3.17-3.01 (m, 2H); 2.95 (s, 3H), 2.94-2.91 (m, 1H); 1.86-1.83 (m, 2H); 1.58-1.54 (m, 2H); 1.50 (s, 9H).

tert-butyl 3-((3-(4-(methylsulfonamido)phenyl)-4-oxo-4H-chromen-7-yl)ethynyl)azetidine-1-carboxylate

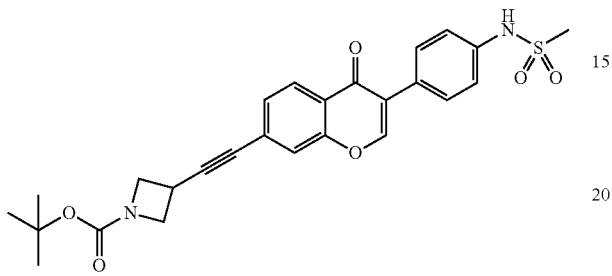

MS found for $C_{26}H_{26}N_2O_6S$ as $(M+H)^+$ 495.03 $^1H$ NMR (400 MHz, dmso-$d_6$): δ: 9.86 (s, 1H); 8.54 (s, 1H); 8.11 (d, J=8.4 Hz, 1H); 7.80 (s, 1H); 7.57-7.52 (m, 3H); 7.27 (d, J=8.4 Hz, 2H), 4.21 (m, 2H); 3.90 (m, 2H); 3.76-3.72 (m, 1H); 3.01 (s, 3H), 1.44 (s, 9H).

N-(4-(4-oxo-7-((tetrahydro-2H-pyran-4-yl)ethynyl)-4H-chromen-3-yl)phenyl)methanesulfonamide

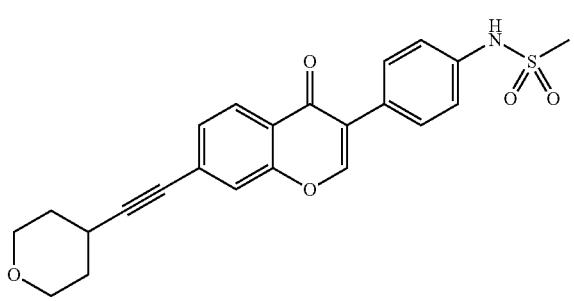 [SMILES: CS(=O)(=O)Nc1ccc(-c2coc3cc(C#CC4CCOCC4)ccc3c2=O)cc1]

MS found for $C_{23}H_{21}NO_5S$ as $(M+H)^+$ 424.10 $^1H$ NMR (400 MHz, dmso-$d_6$): δ: 9.85 (s, 1H); 8.52 (s, 1H); 8.08 (d, J=8.4 Hz, 1H); 7.72 (s, 1H); 7.56-7.47 (m, 3H); 7.26 (d, J=8.4 Hz, 2H), 3.83-3.81 (m, 2H); 3.47-3.42 (m, 2H); 2.97 (s, 3H), 2.96-2.93 (m, 1H); 1.87-1.84 (m, 2H); 1.67-1.61 (m, 2H).

C. Preparation of Other Compounds of Formula I

Similarly, following the procedure of Example 4A, but optionally replacing 3-(4-(methylsulfonamido)phenyl)-4-oxo-4H-chromen-7-yltrifluoromethanesulfonate with other compounds of formula (4), and optionally replacing 2-methylbut-3-yn-2-ol with other alkynes of formula (5), other compounds of Formula I are prepared:

EXAMPLE 5

Alternative Preparation of a Compound of Formula I

A. Preparation of a Compound of Formula I in which $R^1$ is 2-oxo-1,2-dihydropyridin-4-yl, $R^2$ is Methyl, and $R^3$ is Hydrogen

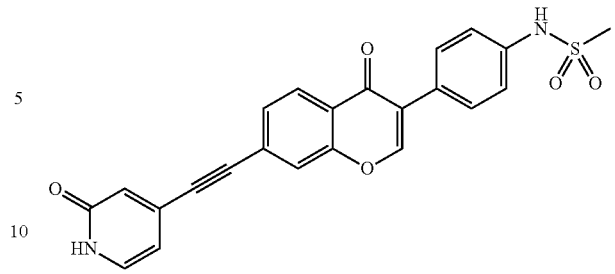

Step 1—Preparation of N-(4-(4-oxo-7-((trimethylsilyl)ethynyl)-4H-chromen-3-yl)phenyl)methanesulfonamide

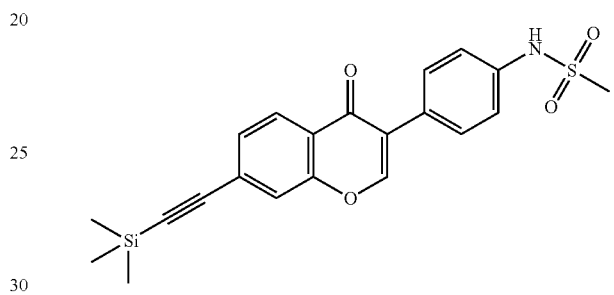

3-(4-(methylsulfonamido)phenyl)-4-oxo-4H-chromen-7-yl trifluoromethanesulfonate (2.5 g, 5.39 mmol), trimethylsilylacetylene (0.92 ml, 1.2 eq), $PdCl_2(PPh_3)_2$ (175 mg, 0.05 eq), copper iodide (28.8 mg 0.03 eq), triphenylphosphine (40 mg 0.03 eq) and triethylamine (3.12 ml, 4.0 eq) were combined in dry tetrahydrofuran (10 ml) and heated in microwave for 30 minutes at 85° C. The reaction mixture was partitioned between ethyl acetate and water, the organic phase dried with magnesium sulfate, and solvent removed under reduced pressure. The crude product was heated in acetonitrile, cooled down and the solids were filtered off. This procedure was repeated twice in order to afford N-(4-(4-oxo-7-((trimethylsilyl)ethynyl)-4H-chromen-3-yl)phenyl)methanesulfonamide.

Step 2—Preparation of N-(4-(7-ethynyl-4-oxo-4H-chromen-3-yl)phenyl)-methanesulfonamide

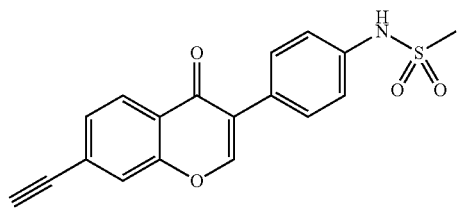 [SMILES: C#Cc1ccc2c(=O)c(-c3ccc(NS(C)(=O)=O)cc3)coc2c1]

N-(4-(4-oxo-7-((trimethylsilyl)ethynyl)-4H-chromen-3-yl)phenyl)methanesulfonamide (1.8 g, 4.37 mmol) was dissolved in a 1:1 mixture of methanol/tetrahydrofuran (6 ml), potassium carbonate (121 mg, 0.2 eq) was added, and the mixture was stirred at room temperature for 1 hour. After the reaction was completed the solvent was removed under reduced pressure, and the residue was extracted with ethyl acetate in the presence of water. The organic phase was dried over magnesium sulfate, filtered, and solvent removed under reduced pressure to afford N-(4-(7-ethynyl-4-oxo-4H-chromen-3-yl)phenyl)methanesulfonamide.

Step 3—Preparation of N-(4-(4-oxo-7-((2-oxo-1,2-dihydropyridin-4-yl)ethynyl)-4H-chromen-3-yl)phenyl)methanesulfonamide

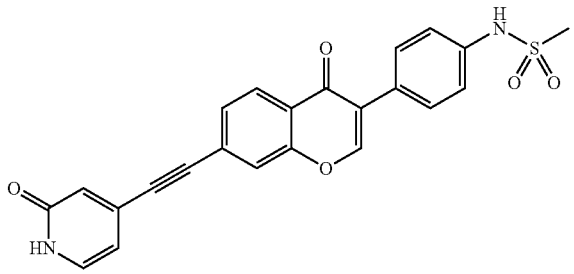 [SMILES: CS(=O)(=O)Nc1ccc(-c2coc3cc(C#Cc4cc[nH]c(=O)c4)ccc3c2=O)cc1]

N-(4-(7-ethynyl-4-oxo-4H-chromen-3-yl)phenyl)methanesulfonamide (100 mg, 0.29 mmol) was combined with 4-bromo-2-tert-butoxypyridine (0.074 mg, 1.1 eq), PdCl$_2$(PPh$_3$)$_2$ (10 mg, 0.05 eq), copper iodide (4 mg 0.002 eq), triphenylphosphine (6 mg 0.03 eq) and triethylamine (0.12 ml, 4.0 eq) in dry tetrahydrofuran (10 ml) and heated in microwave for 30 minutes at 85° C. Solvent was removed from the product under reduced pressure, and the residue was extracted with ethyl acetate in the presence of water. The organic phase was dried over magnesium sulfate, filtered and concentrated under reduced pressure to afford N-(4-(7-((2-tert-butoxypyridin-4-yl)ethynyl)-4-oxo-4H-chromen-3-yl)phenyl)methanesulfonamide. This crude product was dissolved in dichloromethane/trifluoroacetic acid 1:1 (4 ml) and stirred at room temperature for 1 hour. The solvent was removed under reduced pressure, and the residue was extracted with ethyl acetate in the presence of water. The organic phase was dried over magnesium sulfate, filtered and concentrated under reduced pressure. The product was heated in acetonitrile, cooled, and the solids were filtered out. This procedure was repeated twice in order to afford N-(4-(4-oxo-7-((2-oxo-1,2-dihydropyridin-4-yl)ethynyl)-4H-chromen-3-yl)phenyl)methanesulfonamide.

MS found for C$_{23}$H$_{16}$N$_2$O$_5$S as (M+H)$^+$ 433.04 $^1$H NMR (400 MHz, dmso-d$_6$): $^1$H-NMR (DMSO) δ: 11.80 (s, 1H), 9.87 (s, 1H), 8.58 (s, 1H), 8.17 (d, J=8.0 Hz, 1H), 7.98 (s, 1H), 7.67 (d, J=8.0 Hz, 1H), 7.58 (d, J=8.8 Hz, 2H), 7.45 (d, J=6.0 Hz, 1H), 7.27 (d, J=8.8 Hz, 2H), 6.58 (s, 1H), 6.30 (d, J=6.8 Hz, 1H), 3.03 (s, 3H).

B. Preparation of Other Compounds of Formula I

Similarly, following the procedure of Example 5A, Steps 1, 2 and 3, but optionally replacing 4-bromo-2-tert-butoxypyridine with other compounds of formula R$^1$—X, where X is halo, other compounds of Formula I are prepared:

EXAMPLE 6

Alternative Preparation of a Compound of Formula I

A. Preparation of a Compound of Formula I in Which R$^1$ is 1-(cyclopropanecarbonyl)azetidin-3-yl, R$^2$ is Methyl, and R$^3$ is Hydrogen

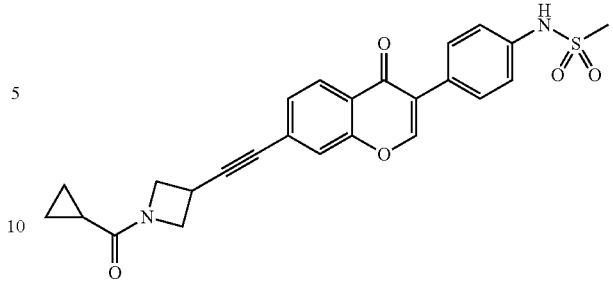

To a solution of tert-butyl 3-((3-(4-(methylsulfonamido)phenyl)-4-oxo-4H-chromen-7-yl)ethynyl)azetidine-1-carboxylate (103 mgs, 0.209 mmol) in dichloromethane (2 mL), trifluoroacetic acid (0.2 mL, 2.08 mmol) was added and stirred at room temperature. After 2 hours the reaction mixture was concentrated and the residue dried under reduced pressure. The crude material was dissolved in dichloromethane (3 mL) and diisopropylethylamine (0.2 mL) and cyclopropanecarbonyl chloride (0.1 mL) were added, and the mixture stirred at room temperature. After 16 hours, the reaction mixture was concentrated under reduced pressure, and the residue dissolved in tetrahydrofuran (2 mL) and 7N ammonia in methanol (4 mL) was added, and the mixture was stirred for 14 hours. The reaction mixture was then concentrated and chromatographed (SiO$_2$, 5% methanol/ethyl acetate) to provide N-(4-(7-((1-(cyclopropanecarbonyl)azetidin-3-yl)ethynyl)-4-oxo-4H-chromen-3-yl)phenyl)methanesulfonamide:

MS found for C$_{25}$H$_{22}$N$_2$O$_5$S as (M+H)$^+$ 463.03 $^1$H NMR (400 MHz, dmso-d$_6$): δ: 9.84 (s, 1H); 8.54 (s, 1H); 8.11 (d, J=8.4 Hz, 1H); 7.80 (s, 1H); 7.57-7.52 (m, 3H); 7.27 (d, J=8.4 Hz, 2H), 4.62 (m, 1H); 4.32-4.20 (m, 2H); 3.90-3.80 (m, 2H); 2.95 (s, 3H), 1.52-1.48 (m, 1H); 0.72-0.68 (m, 4H).

B. Preparation of other Compounds of Formula I

Similarly, following the procedure of Example 6A, but replacing tert-butyl 3-((3-(4-(methylsulfonamido)phenyl)-4-oxo-4H-chromen-7-yl)ethynyl)azetidine-1-carboxylate with of N-(4-(4-oxo-7-(piperidin-4-ylethynyl)-4H-chromen-3-yl)phenyl)methanesulfonamide, the following compound of Formula I was prepared:

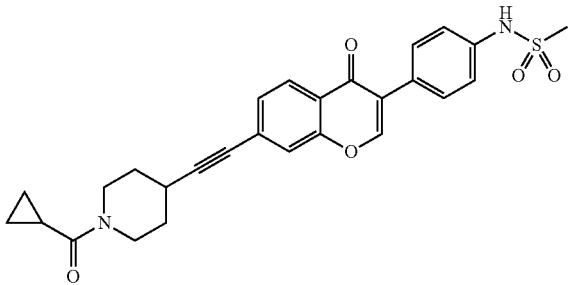

N-(4-(7-((1-(cyclopropanecarbonyl)piperidin-4-yl)ethynyl)-4-oxo-4H-chromen-3-yl)phenyl)methanesulfonamide MS found for C$_{27}$H$_{26}$N$_2$O$_5$S as (M+H)$^+$ 491.1 $^1$H NMR (400 MHz, dmso-d$_6$): δ: 9.84 (s, 1H); 8.52 (s, 1H); 8.08 (d, J=8.4 Hz, 1H); 7.74 (s, 1H); 7.56-7.48 (m, 3H); 7.26 (d, J=8.4 Hz, 2H), 3.93-3.89 (m, 2H); 3.49-3.40 (m, 2H); 3.24-3.15 (m, 1H); 3.03 (s, 3H), 2.00-1.95 (m, 2H); 1.64-1.44 (m, 3H); 0.71-0.68 (m, 4H).

C. Preparation of Other Compounds of Formula I

Similarly, following the procedure of Example 6A, but optionally replacing tert-butyl 3-((3-(4-(methylsulfonamido)phenyl)-4-oxo-4H-chromen-7-yl)ethynyl)azetidine-1-carboxylate with other similar compounds, other compounds of Formula I are prepared:

EXAMPLE 7

Alternative Preparation of a Compound of Formula I

A. Preparation of a Compound of Formula I in Which $R^1$ is Piperidin-4-yl, $R^2$ is Methyl, and $R^3$ is Hydrogen

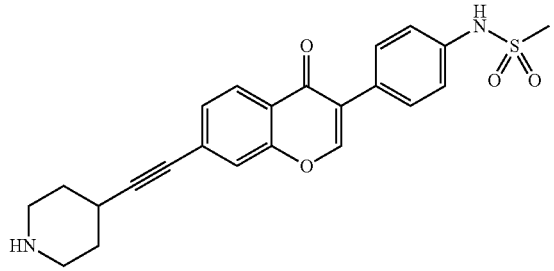 [SMILES: CS(=O)(=O)Nc1ccc(-c2coc3cc(C#CC4CCNCC4)ccc3c2=O)cc1]

To a solution of tert-butyl 4-((3-(4-(methylsulfonamido)phenyl)-4-oxo-4H-chromen-7-yl)ethynyl)piperidine-1-carboxylate (32 mgs, 0.06 mmol) in dichloromethane (1 mL), trifluoroacetic acid (0.05 mL) was added and stirred at room temperature. After 2 hours, the reaction mixture was concentrated under reduced pressure and the residue dried. This trifluoroacetic acid salt was converted to the free amine using MP-Carbonate (4 equiv) in dichloromethane, and the resulting free amine was converted into the corresponding hydrochloride salt of N-(4-(4-oxo-7-(piperidin-4-ylethynyl)-4H-chromen-3-yl)phenyl)methanesulfonamide.

MS found for $C_{23}H_{22}N_2O_4S \cdot HCl$ as $(M+H)^+$ 423.10 $^1H$ NMR (400 MHz, dmso-$d_6$): δ: 11.90 (s, 1H); 9.88 (s, 1H); 8.94 (brs, 1H); 8.54 (s, 1H); 8.09 (d, J=8.4 Hz, $^1H$); 7.76 (s, 1H); 7.56-7.49 (m, 3H); 7.27 (d, J=8.4 Hz, 2H); 3.56-3.36 (m, 4H); 2.96 (s, 3H); 2.94-2.91 (m, 1H); 2.08-2.06 (m, 2H); 1.86-1.83 (m, 2H).

B. Preparation of Other Compounds of Formula I

Similarly, following the procedure of Example 7A, but replacing tert-butyl 4-((3-(4-(methylsulfonamido)phenyl)-4-oxo-4H-chromen-7-yl)ethynyl)piperidine-1-carboxylate with similar compounds, other compounds of Formula I are prepared:

EXAMPLE 8

Alternative Preparation of a Compound of Formula I

A. Preparation of a Compound of Formula I in Which $R^1$ is 1,2-dimethyl-1H-imidazole, $R^2$ is Methyl, and $R^3$ is Hydrogen

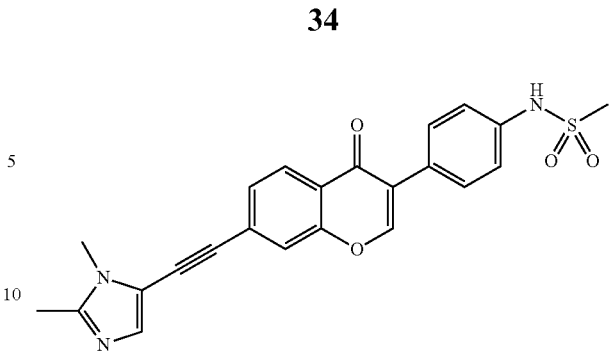

To a stirred mixture of 1,2-dimethyl-1H-imidazole-5-carbaldehyde (645 mgs, 5.2 mmol) and potassium carbonate (1.4 g, 10.4 mmol) in methanol (10 mL) at 0° C. was added dropwise a solution of (1-diazo-2-oxo-propyl)-phosphonic acid dimethyl ester (1 g, 5.2 mmol) in methanol (5 ml). The resulting mixture was slowly warmed to room temperature and stirred overnight. The resulting mixture was then concentrated and chromatographed (SiO$_2$, 5% methanol/ethyl acetate) to provide N-(4-(7-((1,2-dimethyl-1H-imidazol-5-yl)ethynyl)-4-oxo-4H-chromen-3-yl)phenyl)methanesulfonamide. MS found for $C_{23}H_{19}N_3O_4S$ as $(M+H)^+$ 434.1 $^1H$ NMR (400 MHz, dmso-$d_6$): δ: 9.86 (s, 1H); 8.55 (s, 1H); 8.14 (d, J=8.4 Hz, 1H); 7.90 (s, 1H); 7.63-7.56 (m, 3H); 7.29-7.25 (m, 3H), 3.65 (s, 3H); 3.02 (s, 3H); 2.35 (s, 3H).

B. Preparation of Other Compounds of Formula I

Similarly, following the procedure of Example 8A, but replacing 1,2-dimethyl-1H-imidazole-5-carbaldehyde with 1-isopropyl-1H-imidazole-5-carbaldehyde.hydrochloride, the following compound of Formula I was prepared:

N-(4-(7-((1-isopropyl-1H-imidazol-5-yl)ethynyl)-4-oxo-4H-chromen-3-yl)phenyl)methanesulfonamide

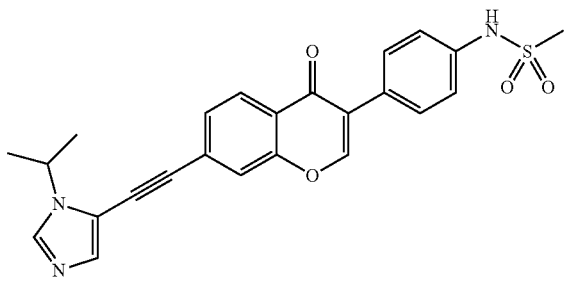 [SMILES: CC(C)n1cncc1C#Cc1ccc2c(=O)c(-c3ccc(NS(C)(=O)=O)cc3)coc2c1]

MS found for $C_{24}H_{21}N_3O_4S$ as $(M+H)^+$ 448.08 $^1H$ NMR (400 MHz, dmso-$d_6$): δ: 9.86 (s, 1H); 8.56 (s, 1H); 8.14 (d, J=8.4 Hz, 1H); 7.97 (s, 1H); 7.91 (s, 1H); 7.63-7.53 (m, 3H); 7.42 (s, 1H); 7.26 (d, J=8.4 Hz, 2H); 4.65 (m, 1H); 3.02 (s, 3H); 1.51 (d, J=6.4 Hz, 6H).

Similarly, replacing 1,2-dimethyl-1H-imidazole-5-carbaldehyde with 1-methyl-1H-imidazole-4-carbaldehyde, the following compound of Formula I was prepared:

N-(4-(7-((1-methyl-1H-imidazol-4-yl)ethynyl)-4-oxo-4H-chromen-3-yl)phenyl)methanesulfonamide

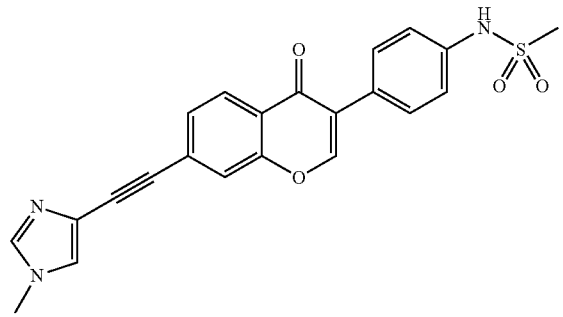 [SMILES: Cn1cnc(C#Cc2ccc3c(=O)c(-c4ccc(NS(C)(=O)=O)cc4)coc3c2)c1]

N-(4-(7-((1-methyl-1H-imidazol-4-yl)ethynyl)-4-oxo-4H-chromen-3-yl)phenyl)methanesulfonamide MS found for $C_{22}H_{17}N_3O_4S$ as $(M+H)^+$ 420.08 $^1$H NMR (400 MHz, dmso-$d_6$): δ: 9.86 (s, 1H); 8.56 (s, 1H); 8.14 (d, J=8.4 Hz, 1H); 7.91 (s, 1H); 7.63-7.53 (m, 5H); 7.26 (d, J=8.4 Hz, 2H); 3.70 (s, 3H); 3.02 (s, 3H).

C. Preparation of Other Compounds of Formula I

Similarly, following the procedure of Example 8A, but replacing 1,2-dimethyl-1H-imidazole-5-carbaldehyde with similar compounds, other compounds of Formula I are prepared:

EXAMPLE 9

Alternative Preparation of a Compound of Formula I

A. Preparation of a Compound of Formula I in which $R^1$ is 1-azetidin-3-yl, $R^2$ is Methyl, and $R^3$ is Hydrogen

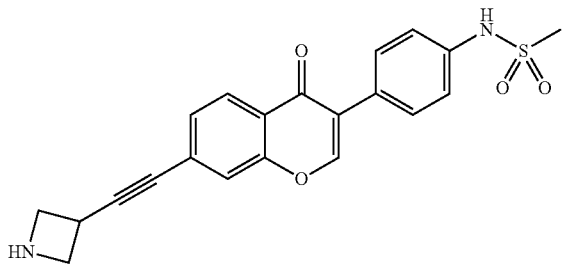 [SMILES: CS(=O)(=O)Nc1ccc(-c2coc3cc(C#CC4CNC4)ccc3c2=O)cc1]

To a solution of tert-butyl 3-((3-(4-(methylsulfonamido)phenyl)-4-oxo-4H-chromen-7-yl)ethynyl)azetidine-1-carboxylate (237 mgs, 0.48 mmol) in dichloromethane (8 mL), trifluoroacetic acid (0.8 mL) was added and the mixture stirred at room temperature. After 2 hours, the reaction mixture was concentrated under reduced pressure, and the residue was triturated with diethylether, filtered and dried to give N-(4-(7-(azetidin-3-ylethynyl)-4-oxo-4H-chromen-3-yl)phenyl)methanesulfonamide as the trifluoroacetic acid salt. MS found for $C_{21}H_{18}N_2O_4S$ as $(M+H)^+$ 395.06 $^1$H NMR (400 MHz, dmso-$d_6$): δ: 9.86 (s, 1H); 8.82 (s, 1H); 8.55 (s, 1H); 8.14 (d, J=8.4 Hz, 1H); 7.78 (s, 1H); 7.56-7.52 (m, 3H); 7.27 (d, J=8.4 Hz, 2H), 4.27-4.24 (m, 2H); 4.09-3.98 (m, 3H); 3.01 (s, 3H).

EXAMPLE 10

Alternative Preparation of a Compound of Formula I

A. Preparation of a Compound of Formula I in Which $R^1$ is Cyclopentylazetidin-1-carboxylate, $R^2$ is Methyl, and $R^3$ is Hydrogen

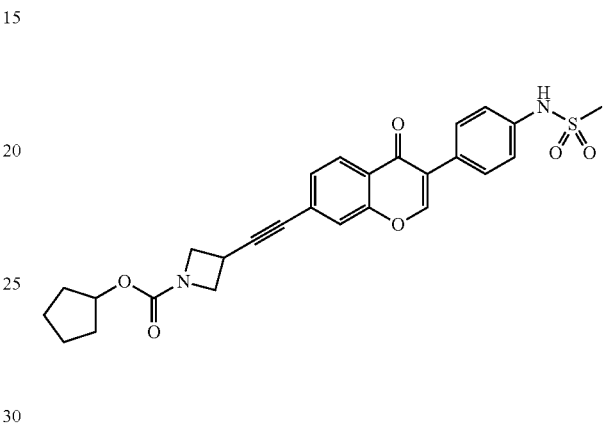

To a mixture of N-(4-(7-(azetidin-3-ylethynyl)-4-oxo-4H-chromen-3-yl)phenyl)methanesulfonamide.trifluoroacetic acid salt (55 mgs, 0.140 mmol) in dichloromethane (3 mL) was added cyclopentyl 2,5-dioxopyrrolidin-1-yl carbonate (95 mgs, 0.42 mmol) and diisopropylethylamine (0.2 mL, 1.4 mmol), and the mixture was stirred at room temperature for 16 hours. The resulting mixture was concentrated under reduced pressure, and chromatographed (SiO$_2$, 25% ethyl acetate/dichloromethane) to provide cyclopentyl-3-((3-(4-(methylsulfonamido)phenyl)-4-oxo-4H-chromen-7-yl)ethynyl)azetidine-1-carboxylate:

MS found for $C_{27}H_{26}N_2O_6S$ as $(M+H)^+$ 507.07 $^1$H NMR (400 MHz, dmso-$d_6$): δ: 9.85 (s, 1H); 8.53 (s, 1H); 8.11 (d, J=8.4 Hz, 1H); 7.56 (s, 1H); 7.54-7.51 (m, 3H); 7.26 (d, J=8.4 Hz, 2H), 4.96 (m, 1H); 4.23-4.19 (m, 2H); 3.94-3.90 (m, 2H); 3.79-3.74 (m, 1H); 3.01 (s, 3H), 1.78-1.50 (m, 8H).

B. Preparation of Other Compounds of Formula I

Similarly, following the procedure of Example 10A, but replacing cyclopentyl 2,5-dioxopyrrolidin-1-yl carbonate with isobutyraldehyde, other compounds of Formula (I) are prepared.

C. Preparation of Other Compounds of Formula I

Similarly, following the procedure of Example 10A, but replacing cyclopentyl 2,5-dioxopyrrolidin-1-yl carbonate with similar compounds, other compounds of Formula (I) are prepared:

EXAMPLE 11

Alternative Preparation of a Compound of Formula I

A. Preparation of a Compound of Formula I in which $R^1$ is 1-Isobutylazetidin-3-yl, $R^2$ is Methyl, and $R^3$ is Hydrogen

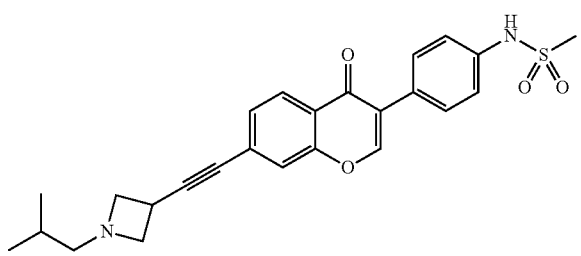 [SMILES: CC(C)CN1CC(C#Cc2ccc3c(=O)c(-c4ccc(NS(C)(=O)=O)cc4)coc3c2)C1]

To a mixture of N-(4-(7-(azetidin-3-ylethynyl)-4-oxo-4H-chromen-3-yl)phenyl)methanesulfonamide.trifluoroacetic acid salt (75 mgs, 0.190 mmol) in 1,2-dichloroethane/tetrahydrofuran (3 mL/0.5 mL), was added isobutyraldehyde (0.03 mL, 0.285 mmol), triethylamine (0.05 mL, 0.38 mmol) and sodium triacetoxyborohydride (60 mgs, 0.285 mmol). The mixture was stirred at room temperature for 16 hours, then the reaction mixture was quenched by adding aqueous 1N sodium hydroxide, and the mixture was extracted with ethyl acetate. The extract was dried over magnesium sulfate, and the solvent was evaporated under reduced pressure. The residue was triturated and washed with diethylether to give N-(4-(7-((1-isobutylazetidin-3-yl)ethynyl)-4-oxo-4H-chromen-3-yl)phenyl)methanesulfonamide:

MS found for $C_{25}H_{26}N_2O_4S$ as $(M+H)^+$ 451.12 $^1H$ NMR (400 MHz, dmso-$d_6$): δ: 8.50 (s, 1H); 8.08 (d, J=8.4 Hz, 1H); 7.72 (s, 1H); 7.52-7.46 (m, 3H); 7.21 (d, J=8.4 Hz, 2H), 3.58-3.55 (m, 2H); 3.49-3.46 (m, 1H); 3.04-3.01 (m, 2H); 2.96 (s, 3H); 2.18 (d, J=6.8 Hz, 2H); 1.52 (m, 1H); 0.83 (d, J=6.8 Hz, 6H).

EXAMPLE 12

Alternative Preparation of a Compound of Formula I

A. Preparation of a Compound of Formula I in Which $R^1$ is 3-Methoxypropanoyl)azetidin-3-yl, $R^2$ is Methyl, and $R^3$ is Hydrogen

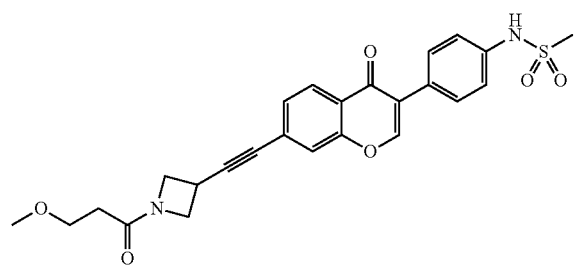

To a mixture of N-(4-(7-(azetidin-3-ylethynyl)-4-oxo-4H-chromen-3-yl)phenyl)methanesulfonamide.trifluoroacetic acid salt (80 mgs, 0.16 mmol), 3-methoxypropanoic acid (0.03 mL, 0.24 mmol), HATU (91 mgs, 0.24 mmol), in N,N-dimethylformamide (1 mL) was added diisopropylethylamine (0.1 mL, 0.41 mmol) and the mixture stirred at room temperature for 16 hours. The reaction mixture was diluted with water and acetonitrile, and the resulting solid was filtered and washed with acetonitrile and ether and dried to give N-(4-(7-((1-(3-methoxypropanoyl)azetidin-3-yl)ethynyl)-4-oxo-4H-chromen-3-yl)phenyl)methanesulfonamide:

MS found for $C_{25}H_{24}N_2O_6S$ as $(M+H)^+$ 481.00 $^1H$ NMR (400 MHz, dmso-$d_6$): δ: 9.85 (s, 1H); 8.53 (s, 1H); 8.10 (d, J=8.4 Hz, 1H); 7.79 (s, 1H); 7.56-7.51 (m, 3H); 7.27 (d, J=8.4 Hz, 2H), 4.46 (m, 1H); 4.21-4.16 (m, 2H); 3.88-3.78 (m, 2H); 3.52-3.49 (m, 2H); 3.20 (s, 3H); 3.01 (s, 3H); 2.30-3.27 (m, 2H).

B. Preparation of other Compounds of Formula I

Similarly, following the procedure of Example 12A, but replacing 3-methoxypropanoic acid with 3,3-difluorocyclobutancarboxylic acid, the following compound of Formula (I) was prepared:

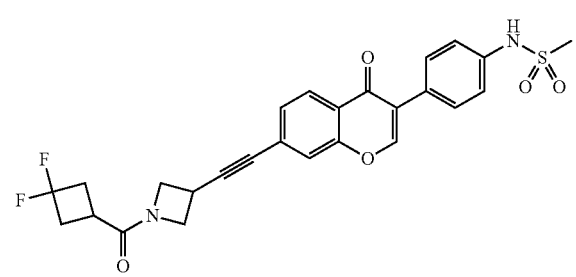 [SMILES: CS(=O)(=O)Nc1ccc(-c2coc3cc(C#CC4CN(C(=O)C5CC(F)(F)C5)C4)ccc3c2=O)cc1]

N-(4-(7-((1-(3,3-difluorocyclobutanecarbonyl)azetidin-3-yl)ethynyl)-4-oxo-4H-chromen-3-yl)phenyl)methanesulfonamide MS found for $C_{26}H_{22}N_2O_5F_2S$ as $(M+H)^+$ 513.03 $^1H$ NMR (400 MHz, dmso-$d_6$): δ: 9.85 (s, 1H); 8.53 (s, 1H); 8.10 (d, J=8.4 Hz, 1H); 7.79 (s, 1H); 7.56-7.51 (m, 3H); 7.27 (d, J=8.4 Hz, 2H), 4.48-4.43 (m, 1H); 4.25-4.18 (m, 2H); 3.94-3.79 (m, 2H); 3.01 (s, 3H); 2.98-2.95 (m. 1H); 2.75-2.65 (m, 4H).

Similarly, following the procedure of Example 12A, but replacing 3-methoxypropanoic acid with 3-(dimethylamino) propanoic acid, the following compound of Formula (I) was prepared:

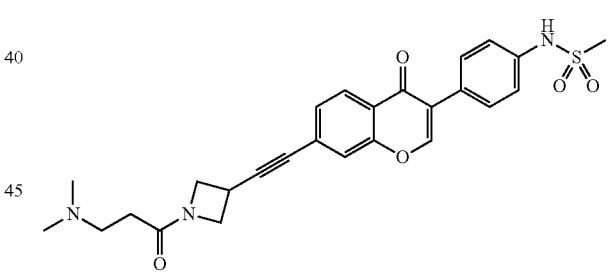

N-(4-(7-((1-(3-(dimethylamino)propanoyl)azetidin-3-yl)ethynyl)-4-oxo-4H-chromen-3-yl)phenyl)methanesulfonamide MS found for $C_{26}H_{27}N_3O_5S$.TFA as $(M+H)^+$ 494.01 $^1H$ NMR (400 MHz, dmso-$d_6$): δ: 9.86 (s, 1H); 9.34 (brs, 8.54 (s, 1H); 8.12 (d, J=8.4 Hz, 1H); 7.77 (s, 1H); 7.56-7.51 (m, 3H); 7.25 (d, J=8.4 Hz, 2H), 4.51-4.47 (m, 1H); 4.27-4.22 (m, 2H); 3.94-3.79 (m, 2H); 3.28-3.23 (m, 2H); 3.01 (s, 3H); 2.76 (s. 6H); 2.62-2.2.56 (m, 2H).

Similarly, following the procedure of Example 12A, the following compounds of Formula (I) were prepared:
N-(4-(7-((1-(2-hydroxypropanoyl)azetidin-3-yl)ethynyl)-4-oxo-4H-chromen-3-yl)phenyl)methanesulfonamide;
N-(4-(7-((1-(1-methylpiperidine-4-carbonyl)azetidin-3-yl) ethynyl)-4-oxo-4H-chromen-3-yl)phenyl)methanesulfonamide;

N-(4-(7-((1-(2,2-difluorocyclopropane-carbonyl)azetidin-3-yl)ethynyl)-4-oxo-4H-chromen-3-yl)phenyl)methanesulfonamide;

N-(4-(7-((1-(cyclobutanecarbonyl)azetidin-3-yl)ethynyl)-4-oxo-4H-chromen-3-yl)phenyl)methanesulfonamide;

N-(4-(7-((1-(1-methylcyclopropanecarbonyl)-azetidin-3-yl)ethynyl)-4-oxo-4H-chromen-3-yl)phenyl)methanesulfonamide;

tert-butyl 1-(3-((3-(4-(methylsulfonamido)-phenyl)-4-oxo-4H-chromen-7-yl)ethynyl)azetidine-1-carbonyl)-cyclobutylcarbamate;

tert-butyl 1-(3-((3-(4-(methylsulfonamido)phenyl)-4-oxo-4H-chromen-7-yl)ethynyl)azetidine-1-carbonyl)cyclopropylcarbamate;

tert-butyl (1-(3-((3-(4-(methylsulfonamido)-phenyl)-4-oxo-4H-chromen-7-yl)ethynyl)azetidine-1-carbonyl)cyclopropyl)-methylcarbamate;

N-(4-(7-((1-(2-hydroxyacetyl)azetidin-3-yl)ethynyl)-4-oxo-4H-chromen-3-yl)phenyl)methanesulfonamide;

N-(4-(7-((1-(3-hydroxy-3-methylcyclobutane-carbonyl)azetidin-3-yl)ethynyl)-4-oxo-4H-chromen-3-yl)phenyl)methanesulfonamide;

N-(4-(7-((1-(2-hydroxy-2-methylpropanoyl)-azetidin-3-yl)ethynyl)-4-oxo-4H-chromen-3-yl)phenyl)methanesulfonamide; and N-(4-(7-((1-(3-methyloxetane-3-carbonyl)azetidin-3-yl)ethynyl)-4-oxo-4H-chromen-3-yl)phenyl)methanesulfonamide.

C. Preparation of Other Compounds of Formula I

Similarly, following the procedure of Example 12A, but replacing 3-methoxypropanoic acid with other carboxylic acids, other compounds of Formula (I) are prepared.

FORMULATION EXAMPLES

The following sample formulations are illustrative and do not reflect the full scope of active ingredient amounts or excipient amounts that may be combined to provide a specific tablet, capsule, inhaler, or other drug presentation.

EXAMPLE 13

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 14

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 15

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 16

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 17

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 18

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 19

A subcutaneous formulation may be prepared as follows:

| Ingredient | Quantity |
| --- | --- |
| Active Ingredient | 5.0 mg |
| Corn Oil | 1.0 mL |

EXAMPLE 20

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 21

A topical preparation is prepared having the following composition:

| Ingredients | grams |
| --- | --- |
| Active ingredient | 0.01-1.0 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 22

Sustained Release Composition

| Ingredient | Weight Range (%) | Preferred Range (%) | Most Preferred |
| --- | --- | --- | --- |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have hardness sufficient to withstand 8 KP compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 23

ALDH2 Assays

Standard ALDH2 reaction mixtures contained 150 uM formaldehyde, 2.5 mM NAD$^+$, 10 mM MgCl2 and 10 nM recombinant human ALDH2 in 50 mM Hepes buffer, pH 7.4, 0.01% Tween 20 in a final volume of 50 ul using 384-well plates. After 60 min of pre-incubation of compound with ALDH2 and formaldehyde, the reaction was started by adding NAD+ and the reaction mixture was allowed to proceed for 90 minutes. Activity of the enzyme was determined by monitoring NADH formation using Perkin-Elmer Envision Reader with excitation and emission wavelengths set at 340 and 460 nm, respectively.

MAO-A and MAO-B Assays

MAO assays included luminogenic MAO substrate, reaction buffers, Luciferin Detection and the reconstitution buffer with esterase. Standard MAO reaction mixtures included microsome contained MAO-A (2 ug) or MAO-B (10 ug), 160 uM substrate for MAO-A or 16 uM substrate for MAO-B, MAO-A buffer (100 mM Hepes buffer, pH 7.5, 5% glycerol) or MAO-B buffer (100 mM Hepes, pH 7.5, 5% glycerol, 10% dimethyl sulfoxide) in a final volume of 30 ul. After 20 minutes of pre-incubation of the enzyme with compounds, the reaction was initiated by adding enzyme substrate and the reaction was allowed to proceed for 60 minutes. Reconstituted Luciferin Detection Reagent (30 ul) was then added is added to simultaneously stop the MAO reaction and convert the methyl ester derivative to luciferin and produce light. The amount of light produced is directly proportional to the activity of MAO. The mixtures were further incubated for 20 minutes and activity of the enzyme was determined using Perkin-Elmer Envision Reader.

Note: IC50 refers to the concentration of a compound that inhibits a reaction by 50%. In the case of competitive inhibition, $IC_{50}=2Ki$ when the substrate is present at the Km concentration, as per the relationship:

$$Ki=IC50/[1+(\text{substrate concentration}/Km)].$$

Representative data for several compounds of the invention are presented in Table 1 below.

| COMPOUND | $IC_{50}$ hALDH2 (nM) | $IC_{50}$ hMAO-A | $IC_{50}$ hMAO-B |
|---|---|---|---|
| N-(4-(7-(cyclopropylethynyl)-4-oxo-4H-chromen-3-yl)phenyl)methanesulfonamide; | 57.7 | >13,000 | >13,000 |
| N-(4-(4-oxo-7-(phenylethynyl)-4H-chromen-3-yl)phenyl)methanesulfonamide | 329 | >13,000 | >13,000 |
| N-(4-(7-(3-hydroxy-3-methylbut-1-ynyl)-4-oxo-4H-chromen-3-yl)phenyl)methanesulfonamide | 2181 | >91,000 | >91,000 |
| N-(4-(7-((1-methyl-1H-imidazol-5-yl)ethynyl)-4-oxo-4H-chromen-3-yl)phenyl)methane-sulfonamide | <4.9 | >130,000 | 365 |
| N-(4-(7-(3-methoxyprop-1-ynyl)-4-oxo-4H-chromen-3-yl)phenyl)methanesulfonamide | 47 | >130,000 | >130,000 |
| N-(4-(7-((1-hydroxycyclohexyl)ethynyl)-4-oxo-4H-chromen-3-yl)phenyl)methanesulfonamide | 1706 | >130,000 | >130,000 |
| N-(4-(7-((1-aminocyclohexyl)ethynyl)-4-oxo-4H-chromen-3-yl)phenyl)methanesulfonamide | 528 | >130,000 | >130,000 |
| N-(4-(4-oxo-7-(pyridin-2-ylethynyl)-4H-chromen-3-yl)phenyl)methanesulfonamide | 90 | >130,000 | >130,000 |
| N-(4-(7-((1-hydroxycyclopentyl)ethynyl)-4-oxo-4H-chromen-3-yl)phenyl)methane-sulfonamide | 386 | >130,000 | >130,000 |
| N-(4-(4-oxo-7-(pyrimidin-5-ylethynyl)-4H-chromen-3-yl)phenyl)methanesulfonamide | 57 | >130,000 | 114,002 |
| N-(4-(4-oxo-7-(pyridin-3-ylethynyl)-4H-chromen-3-yl)phenyl)methanesulfonamide | 21 | >130,000 | >130,000 |
| N-(4-(7-(3-methoxyprop-1-ynyl)-4-oxo-4H-chromen-3-yl)phenyl)cyclopropanesulfonamide | 96 | >130,000 | >130,000 |
| N-(4-(7-((1-hydroxycyclopentyl)ethynyl)-4-oxo-4H-chromen-3-yl)phenyl)methanesulfonamide | 156 | >130,000 | >130,000 |
| tert-butyl 4-((3-(4-(methylsulfonamido)phenyl)-4-oxo-4H-chromen-7-yl)ethynyl)piperidine-1-carboxylate | 86 | >130,000 | >130,000 |
| tert-butyl 3-((3-(4-(methylsulfonamido)phenyl)-4-oxo-4H-chromen-7-yl)ethynyl)azetidine-1-carboxylate | 9 | >130,000 | >130,000 |
| N-(4-(4-oxo-7-((2-oxo-1,2-dihydropyridin-4-yl)ethynyl)-4H-chromen-3-yl)phenyl)methanesulfonamide | 9 | >130,000 | >130,000 |
| N-(4-(7-((1-(cyclopropanecarbonyl)azetidin-3-yl)ethynyl)-4-oxo-4H-chromen-3-yl)phenyl)methanesulfonamide | 5 | >130,000 | >130,000 |
| N-(4-(4-oxo-7-(piperidin-4-ylethynyl)-4H-chromen-3-yl)phenyl)methanesulfonamide | 174 | >109,587 | >130,000 |
| N-(4-(7-((1-(cyclopropanecarbonyl)piperidin-4-yl)ethynyl)-4-oxo-4H-chromen-3-yl)phenyl)methanesulfonamide | 6.5 | >130,000 | >130,000 |

-continued

| COMPOUND | IC$_{50}$ hALDH2 (nM) | IC$_{50}$ hMAO-A | IC$_{50}$ hMAO-B |
|---|---|---|---|
| N-(4-(7-((1,2-dimethyl-1H-imidazol-5-yl)ethynyl)-4-oxo-4H-chromen-3-yl)phenyl)methanesulfonamide | 15 | >130,000 | >130,000 |
| N-(4-(7-((1-isopropyl-1H-imidazol-5-yl)ethynyl)-4-oxo-4H-chromen-3-yl)phenyl)methanesulfonamide | 7 | >130,000 | >130,000 |
| N-(4-(7-((1-methyl-1H-imidazol-4-yl)ethynyl)-4-oxo-4H-chromen-3-yl)phenyl)methanesulfonamide | 95 | >86479 | >130,000 |
| N-(4-(7-(azetidin-3-ylethynyl)-4-oxo-4H-chromen-3-yl)phenyl)methanesulfonamide | 266 | >130,000 | >94402 |
| cyclopentyl 3-((3-(4-(methylsulfonamido)phenyl)-4-oxo-4H-chromen-7-yl)ethynyl)azetidine-1-carboxylate | 9 | >130,000 | >130,000 |
| N-(4-(4-oxo-7-((tetrahydro-2H-pyran-4-yl)ethynyl)-4H-chromen-3-yl)phenyl)methanesulfonamide | 43 | >130,000 | >130,000 |
| N-(4-(7-((1-isobutylazetidin-3-yl)ethynyl)-4-oxo-4H-chromen-3-yl)phenyl)methane-sulfonamide | 109 | >130,000 | >130,000 |
| N-(4-(7-((1-(3-methoxypropanoyl)azetidin-3-yl)ethynyl)-4-oxo-4H-chromen-3-yl)phenyl)methanesulfonamide | 8 | >130,000 | >130,000 |
| N-(4-(7-((1-(3,3-difluorocyclobutanecarbonyl)-azetidin-3-yl)ethynyl)-4-oxo-4H-chromen-3-yl)phenyl)methanesulfonamide | 6 | >130,000 | >130,000 |
| N-(4-(7-((1-(3-(dimethylamino)propanoyl)-azetidin-3-yl)ethynyl)-4-oxo-4H-chromen-3-yl)phenyl)methanesulfonamide | 64 | 46947 | >130,000 |
| N-(4-(7-((1-(2-hydroxyacetyl)azetidin-3-yl)ethynyl)-4-oxo-4H-chromen-3-yl)phenyl)methanesulfonamide | 15 | >130,000 | >130,000 |
| N-(4-(7-((1-(3-hydroxy-3-methylcyclobutane-carbonyl)azetidin-3-yl)ethynyl)-4-oxo-4H-chromen-3-yl)phenyl)methanesulfonamide | 5 | >130,000 | >130,000 |
| N-(4-(7-((1-(2-hydroxy-2-methylpropanoyl)-azetidin-3-yl)ethynyl)-4-oxo-4H-chromen-3-yl)phenyl)methanesulfonamide | 16 | >130,000 | >130,000 |
| N-(4-(7-((1-(3-methyloxetane-3-carbonyl)azetidin-3-yl)ethynyl)-4-oxo-4H-chromen-3-yl)phenyl)methanesulfonamide | 6 | >130,000 | >130,000 |
| N-(4-(7-((1-(2-hydroxypropanoyl)azetidin-3-yl)ethynyl)-4-oxo-4H-chromen-3-yl)phenyl)methanesulfonamide | 15 | >130,000 | >130,000 |
| N-(4-(7-((1-(1-methylpiperidine-4-carbonyl)azetidin-3-yl)ethynyl)-4-oxo-4H-chromen-3-yl)phenyl)methanesulfonamide | 35 | >130,000 | >130,000 |
| N-(4-(7-((1-(2,2-difluorocyclopropane-carbonyl)azetidin-3-yl)ethynyl)-4-oxo-4H-chromen-3-yl)phenyl)methanesulfonamide | 5 | >130,000 | >130,000 |
| N-(4-(7-((1-(cyclobutanecarbonyl)azetidin-3-yl)ethynyl)-4-oxo-4H-chromen-3-yl)phenyl)methanesulfonamide | 4 | >130,000 | >130,000 |
| N-(4-(7-((1-(1-methylcyclopropanecarbonyl)-azetidin-3-yl)ethynyl)-4-oxo-4H-chromen-3-yl)phenyl)methanesulfonamide | 6 | >130,000 | >130,000 |
| tert-butyl 1-(3-((3-(4-(methylsulfonamido)-phenyl)-4-oxo-4H-chromen-7-yl)ethynyl)azetidine-1-carbonyl)-cyclobutylcarbamate | 6 | >130,000 | >130,000 |
| tert-butyl 1-(3-((3-(4-(methylsulfonamido)phenyl)-4-oxo-4H-chromen-7-yl)ethynyl)azetidine-1-carbonyl)cyclopropylcarbamate | 5 | 110381 | >130,000 |
| tert-butyl (1-(3-((3-(4-(methylsulfonamido)-phenyl)-4-oxo-4H-chromen-7-yl)ethynyl)azetidine-1-carbonyl)cyclopropyl)-methylcarbamate | 2.3 | >130,000 | >130,000 |

The above data suggests that compounds of the invention generally inhibit the ALDH$_2$ enzyme with an IC$_{50}$ of less than 1 uM.

EXAMPLE 24

Reduction of Cocaine Dependency and Relapse

Intravenous cocaine (0.35 mg/kg/inj) is used in an operant self administration and reinstatement model in rats. In this model, rats addicted to cocaine repeatedly press a lever to obtain an intravenous dose (iv) of cocaine. When cocaine is removed, rats stopped pressing the lever. However, rats resume lever pressing for cocaine (reinstatement) if subjected to a small intraperitoneal (ip) dose (10 mg/kg) of cocaine that normally has no effect in naïve animals. This is a valid animal model of relapse in cocaine addicted humans, and tests the ability of compounds of Formula (I) to block cocaine craving and relapse.

Male Sprague-Dawley rats with jugular vein catheterization are used. Rats are presented with a choice of two levers in the test/training chamber. Depression of the active lever results in delivery of a cocaine reinforcer, while depression of the inactive lever does not result in reinforcement. During the initial 15 hour fixed ratio (FR) 1 training session (FR1 stands for one lever press equals one reinforcement delivery), a food pellet is taped to the active lever to facilitate lever pressing, and each active lever press results in the delivery of a single 45 mg food pellet (Noyes, Lancaster, N.H.). The following day the reinforcer is switched to FR1 lever pressing for cocaine (0.35 mg/kg/inj, delivered in 0.27 sec). Cocaine reinforcement is delivered on a modified FR1 schedule such that each drug infusion is accompanied by illumination of a stimulus over the active lever and a 20 second timeout during which active lever presses are counted but do not result in reinforcer delivery. After 20 seconds the stimulus light turns off and the first lever press again results in drug delivery. Depression of the inactive lever does not have any consequence. Daily training sessions for each group lasts 2 hours, or until a subject earns 200 drug infusions, whichever comes first. The subjects remain in drug self-administration training mode until acquisition criterion is met (average presses on the active lever varies by <10% over 3 consecutive training days). This typically takes 10-14 days.

Extinction and Reinstatement

For extinction and reinstatement experiments, rats are required to display stable responding (variability not higher than 15% in 2 consecutive sessions) on the FR1 schedule of reinforcement. After achieving this criteria, extinction procedures begin such that lever presses no longer resulted in delivery of the reinforcer. When average responding across three consecutive extinction sessions falls to 15% of responding during maintenance, subjects are tested for reinstatement. In cocaine-experienced animals, reinstatement is primed with a non-contingent injection of cocaine (10 mg/kg ip) immediately before the reinstatement session. In order to increase statistical power and therefore decrease animal usage, a second extinction period is initiated 3-4 days after the first, which allowed for additional within-subjects comparisons. Experiments use a between-session-training and testing method in which animals are trained to self administer drug. Their behavior is then extinguished and then reinstatement is primed on different days.

Compound Preparation

Compound in Example 6A was suspended in vehicle (Formulation 2B: 25% PEG400/5% Vit E TPGS/1% SLS, 0.5% Methocel, 69% water) and administered to rats via the oral (p.o.) route in a volume of 4 ml/kg. Cocaine hydrochloride was purchased from Sigma-Aldrich (St. Louis, Mo.). Cocaine was self-administered via the intravenous (i.v.) route in a volume of 0.05 ml/infusion.

Results

Effect of Compounds of Formula (I)

The compounds of Formula (I) are believed to reduce cocaine dependency and relapse. For example, the compound of Example 6A reduced cocaine dependency by 70%, 60% and 87% respectively at doses of 2.5 mg/Kg (2 hour pre-treatment), 5.0 mg/Kg (2 hour pre-treatment) and 10.0 mg/kg (1 hour pre-treatment) respectively as measured by reduction in the average presses of the active lever.

What is claimed is:

1. A compound of Formula I:

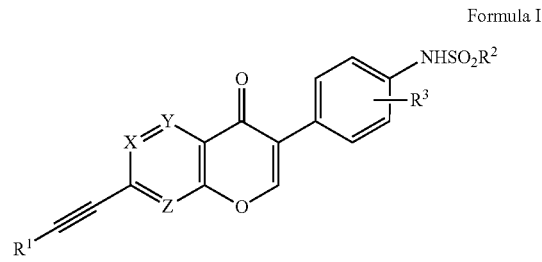

Formula I wherein:
R$^1$ is optionally substituted alkyl, optionally substituted cycloalkyl, optionally substituted heterocyclyl, optionally substituted heteroaryl, or optionally substituted phenyl;
R$^2$ is hydrogen, optionally substituted alkyl, optionally substituted cycloalkyl, or optionally substituted phenyl;
R$^3$ is hydrogen, cyano, optionally substituted amino, alkyl, alkoxy, or halo; and
X, Y and Z are chosen from —CR$^4$—, in which R$^4$ is hydrogen, alkyl, lower alkoxy, or halo;
or a pharmaceutically acceptable salt thereof.

2. The compound of claim 1, wherein R$^1$ is optionally substituted alkyl and R$^2$ is optionally substituted alkyl or optionally substituted cycloalkyl.

3. The compound of claim 2, wherein R$^1$ is alkyl of 1-6 carbon atoms optionally substituted by halo, hydroxyl, cyano, optionally substituted alkoxy of 1-6 carbon atoms, optionally substituted acyl, optionally substituted amino, optionally substituted carboxylalkyl, optionally substituted carboxylcycloalkyl, or optionally substituted alkoxycarbonylamino.

4. The compound of claim 3, wherein X, Y and Z are —CR$^4$— and R$^3$ is hydrogen, selected from the group consisting of:
N-(4-(7-(3-methoxyprop-1-ynyl)-4-oxo-4H-chromen-3-yl)phenyl)methanesulfonamide;
N-(4-(7-(3-hydroxy-3-methylbut-1-ynyl)-4-oxo-4H-chromen-3-yl)phenyl)methanesulfonamide; and
N-(4-(7-(3-methoxyprop-1-ynyl)-4-oxo-4H-chromen-3-yl)phenyl)cyclopropane-sulfonamide.

5. The compound of claim 1, wherein R$^1$ is optionally substituted cycloalkyl and R$^2$ is optionally substituted alkyl or optionally substituted cycloalkyl.

6. The compound of claim 5, wherein R$^1$ is cycloalkyl optionally substituted by halo, hydroxyl, cyano, alkoxy, optionally substituted acyl, optionally substituted amino, optionally substituted carboxylalkyl, optionally substituted carboxylcycloalkyl, or optionally substituted alkoxycarbonylamino.

7. A compound of claim 6, wherein X, Y and Z are —$CR^4$— and $R^3$ is hydrogen.

8. A compound of claim 1, selected from the group consisting of:
- N-(4-(7-(cyclopropylethynyl)-4-oxo-4H-chromen-3-yl)phenyl)methanesulfonamide;
- N-(4-(7-(((1S,2R)-2-hydroxycyclopentyl)ethynyl)-4-oxo-4H-chromen-3-yl)phenyl)methanesulfonamide;
- N-(4-(7-((1-hydroxycyclopentyl)ethynyl)-4-oxo-4H-chromen-3-yl)phenyl)methanesulfonamide;
- N-(4-(7-((1-aminocyclohexyl)ethynyl)-4-oxo-4H-chromen-3-yl)phenyl)methanesulfonamide; and
- N-(4-(7-((1-hydroxycyclohexyl)ethynyl)-4-oxo-4H-chromen-3-yl)phenyl)methanesulfonamide.

9. A compound of claim 1, wherein $R^1$ is optionally substituted heteroaryl and $R^2$ is optionally substituted alkyl or optionally substituted cycloalkyl.

10. A compound of claim 9, wherein $R^1$ is heteroaryl optionally substituted by, halo, hydroxyl, cyano, alkoxy, optionally substituted acyl, optionally substituted amino, optionally substituted carboxylalkyl, optionally substituted carboxylcycloalkyl, or optionally substituted alkoxycarbonylamino.

11. A compound of claim 10, wherein X, Y and Z are —$CR^4$— and $R^3$ is hydrogen.

12. A compound of claim 11, selected from the group consisting of:
- N-(4-(4-oxo-7-(pyrimidin-5-ylethynyl)-4H-chromen-3-yl)phenyl)methanesulfonamide;
- N-(4-(4-oxo-7-(pyridin-2-ylethynyl)-4H-chromen-3-yl)phenyl)methanesulfonamide;
- N-(4-(4-oxo-7-(pyridin-3-ylethynyl)-4H-chromen-3-yl)phenyl)methanesulfonamide;
- N-(4-(7-((1-methyl-1H-imidazol-5-yl)ethynyl)-4-oxo-4H-chromen-3-yl)phenyl)methanesulfonamide.
- N-(4-(7-((1,2-dimethyl-1H-imidazol-5-yl)ethynyl)-4-oxo-4H-chromen-3-yl)phenyl)methanesulfonamide;
- N-(4-(7-((1-methyl-1H-imidazol-4-yl)ethynyl)-4-oxo-4H-chromen-3-yl)phenyl)methanesulfonamide; and
- N-(4-(7-((1-methyl-1H-imidazol-4-yl)ethynyl)-4-oxo-4H-chromen-3-yl)phenyl)methanesulfonamide.

13. The compound of claim 1, wherein $R^1$ is optionally substituted phenyl, $R^2$ is optionally substituted alkyl or optionally substituted cycloalkyl, and $R^3$ is hydrogen.

14. A compound of claim 13, wherein $R^1$ is phenyl and $R^2$ is methyl, namely N-(4-(4-oxo-7-(phenylethynyl)-4H-chromen-3-yl)phenyl)methanesulfonamide.

15. A compound of claim 13, wherein $R^1$ is optionally substituted heterocyclyl and $R^2$ is optionally substituted alkyl or optionally substituted cycloalkyl.

16. A compound of claim 15, wherein X, Y and Z are —$CR^4$— and $R^3$ is hydrogen.

17. A compound of claim 13, wherein $R^1$ is optionally substituted piperidine or optionally substituted tetrahydropyran.

18. A compound of claim 17 selected from the group consisting of:
- tert-butyl 4-((3-(4-(methylsulfonamido)phenyl)-4-oxo-4H-chromen-7-yl)ethynyl)piperidine-1-carboxylate;
- N-(4-(4-oxo-7-(piperidin-4-ylethynyl)-4H-chromen-3-yl)phenyl)methanesulfonamide;
- N-(4-(7-((1-(cyclopropanecarbonyl)piperidin-4-yl)ethynyl)-4-oxo-4H-chromen-3-yl)phenyl)methanesulfonamide; and
- N-(4-(4-oxo-7-((tetrahydro-2H-pyran-4-yl)ethynyl)-4H-chromen-3-yl)phenyl)methanesulfonamide.

19. A compound of claim 17, wherein $R^1$ is azetidine.

20. A compound of claim 19, wherein $R^2$ is methyl, namely N-(4-(7-(azetidin-3-ylethynyl)-4-oxo-4H-chromen-3-yl)phenyl)methanesulfonamide.

21. A compound of claim 17, wherein $R^1$ is N-substituted azetidine, wherein the N-substitution is chosen from optionally substituted alkyl of 1-6 carbon atoms, optionally substituted acyl, optionally substituted amino, optionally substituted carboxylalkyl, optionally substituted carboxylcycloalkyl, and optionally substituted alkoxycarbonylamino.

22. A compound selected from the group consisting of:
- tert-butyl 3-((3-(4-(methylsulfonamido)phenyl)-4-oxo-4H-chromen-7-yl)ethynyl)azetidine-1-carboxylate;
- N-(4-(7-(1-(cyclopropanecarbonyl)azetidin-3-yl)ethynyl)-4-oxo-4H-chromen-3-yl)phenyl)methanesulfonamide;
- N-(4-(7-(azetidin-3-ylethynyl)-4-oxo-4H-chromen-3-yl)phenyl)methanesulfonamide;
- cyclopentyl 3-((3-(4-(methylsulfonamido)phenyl)-4-oxo-4H-chromen-7-yl)ethynyl)azetidine-1-carboxylate;
- N-(4-(7-((1-isobutylazetidin-3-yl)ethynyl)-4-oxo-4H-chromen-3-yl)phenyl)methanesulfonamide;
- N-(4-(7-((1-(3-methoxypropanoyl)azetidin-3-yl)ethynyl)-4-oxo-4H-chromen-3-yl)phenyl)methanesulfonamide;
- N-(4-(7-((1-(3,3-difluorocyclobutanecarbonyl)-azetidin-3-yl)ethynyl)-4-oxo-4H-chromen-3-yl)phenyl)methanesulfonamide;
- N-(4-(7-((1-(3-(dimethylamino)propanoyl)-azetidin-3-yl)ethynyl)-4-oxo-4H-chromen-3-yl)phenyl)methanesulfonamide;
- N-(4-(7-((1-(2-hydroxyacetyl)azetidin-3-yl)ethynyl)-4-oxo-4H-chromen-3-yl)phenyl)methanesulfonamide;
- N-(4-(7-((1-(3-hydroxy-3-methylcyclobutane-carbonyl)azetidin-3-yl)ethynyl)-4-oxo-4H-chromen-3-yl)phenyl)methanesulfonamide;
- N-(4-(7-((1-(2-hydroxy-2-methylpropanoyl)-azetidin-3-yl)ethynyl)-4-oxo-4H-chromen-3-yl)phenyl)methanesulfonamide;
- N-(4-(7-((1-(3-methyloxetane-3-carbonyl)azetidin-3-yl)ethynyl)-4-oxo-4H-chromen-3-yl)phenyl)methanesulfonamide;
- N-(4-(7-((1-(2-hydroxypropanoyl)azetidin-3-yl)ethynyl)-4-oxo-4H-chromen-3-yl)phenyl)methanesulfonamide;
- N-(4-(7-((1-(1-methylpiperidine-4-carbonyl)azetidin-3-yl)ethynyl)-4-oxo-4H-chromen-3-yl)phenyl)methanesulfonamide;
- N-(4-(7-((1-(2,2-difluorocyclopropane-carbonyl)azetidin-3-yl)ethynyl)-4-oxo-4H-chromen-3-yl)phenyl)methanesulfonamide;
- N-(4-(7-((1-(cyclobutanecarbonyl)azetidin-3-yl)ethynyl)-4-oxo-4H-chromen-3-yl)phenyl)methanesulfonamide;
- N-(4-(7-((1-(1-methylcyclopropanecarbonyl)-azetidin-3-yl)ethynyl)-4-oxo-4H-chromen-3-yl)phenyl)methanesulfonamide;

tert-butyl 1-(3-((3-(4-(methylsulfonamido)-phenyl)-4-oxo-4H-chromen-7-yl)ethynyl)azetidine-1-carbonyl)-cyclobutylcarbamate;

N-(4-(4-oxo-7-((tetrahydro-2H-pyran-4-yl)ethynyl)-4H-chromen-3-yl)phenyl)methanesulfonamide;

tert-butyl 1-(3-((3-(4-(methylsulfonamido)phenyl)-4-oxo-4H-chromen-7-yl)ethynyl)azetidine-1-carbonyl)cyclopropylcarbamate; and tert-butyl (1-(3-((3-(4-(methylsulfonamido)-phenyl)-4-oxo-4H-chromen-7-yl)ethynyl)azetidine-1-carbonyl)cyclopropyl)-methylcarbamate.

23. The compound of formula:

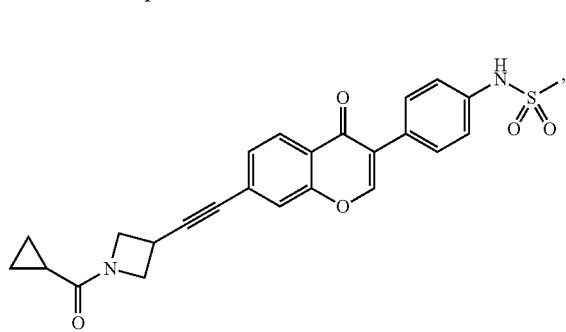

also known as N-(4-(7-((1-(cyclopropanecarbonyl)azetidin-3-yl)ethynyl)-4-oxo-4H-chromen-3-yl)phenyl)methanesulfonamide, or a pharmaceutically acceptable salt thereof.

24. The compound of formula:

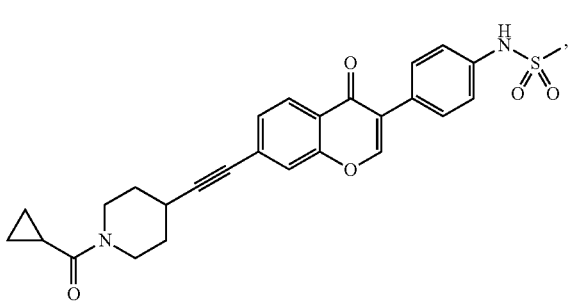

also known as N-(4-(7-((1-(cyclopropanecarbonyl)piperidin-4-yl)ethynyl)-4-oxo-4H-chromen-3-yl)phenyl)methanesulfonamide, or a pharmaceutically acceptable salt thereof.

25. The compound of formula:

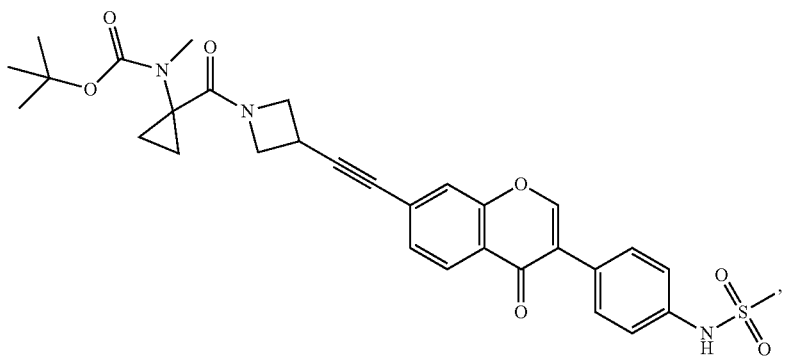

also known as tert-butyl (1-(3-((3-(4-(methylsulfonamido)-phenyl)-4-oxo-4H-chromen-7-yl)ethynyl)azetidine-1-carbonyl)cyclopropyl)-methylcarbamate, or a pharmaceutically acceptable salt thereof.

26. The compound of formula

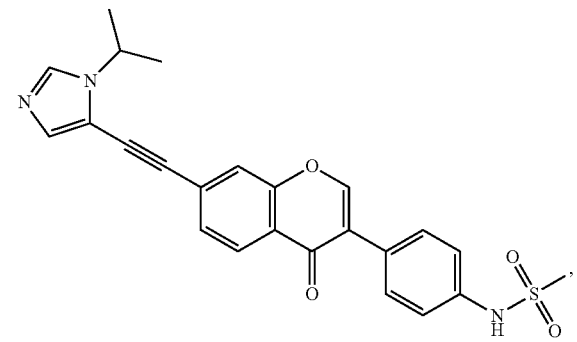

also known as N-(4-(7-((1-isopropyl-1H-imidazol-5-yl)ethynyl)-4-oxo-4H-chromen-3-yl)phenyl)methanesulfonamide, or a pharmaceutically acceptable salt thereof.

27. A pharmaceutical composition comprising a therapeutically effective amount of a compound according to any one of claims 1 to 26 and one or more pharmaceutically acceptable carriers.

28. A method of treating chemical dependency on a dopamine-producing agent selected from the group consisting of cocaine, opiates, amphetamines, nicotine, food and alcohol, comprising administering a therapeutically effective amount of a compound according to any one of claims 1 to 26 to a patient in need thereof.

29. The method of claim 28, wherein the dopamine-producing agent is cocaine.

30. The method of claim 28, wherein the dopamine-producing agent is nicotine.

* * * * *